US010064634B2

(12) United States Patent
Song

(10) Patent No.: US 10,064,634 B2
(45) Date of Patent: *Sep. 4, 2018

(54) CUSTOMIZED ARTHROPLASTY CUTTING GUIDES AND SURGICAL METHODS USING THE SAME

(71) Applicant: Howmedica Osteonics Corporation, Mahwah, NJ (US)

(72) Inventor: Keun Song, Palo Alto, CA (US)

(73) Assignee: Howmedica Osteonics Corporation, Mahwah, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/788,478

(22) Filed: Oct. 19, 2017

(65) Prior Publication Data

US 2018/0036018 A1 Feb. 8, 2018

Related U.S. Application Data

(63) Continuation of application No. 15/195,639, filed on Jun. 28, 2016, now Pat. No. 9,814,475, which is a continuation of application No. 13/749,095, filed on Jan. 24, 2013, now Pat. No. 9,402,637.

(60) Provisional application No. 61/712,577, filed on Oct. 11, 2012.

(51) Int. Cl.
*A61B 17/17* (2006.01)
*A61B 17/15* (2006.01)
*A61B 17/56* (2006.01)

(52) U.S. Cl.
CPC ........ *A61B 17/1764* (2013.01); *A61B 17/157* (2013.01); *A61B 2017/568* (2013.01); *F04C 2270/041* (2013.01)

(58) Field of Classification Search
CPC ..... A61B 17/17; A61B 17/1764; A61B 17/15; A61B 17/157
See application file for complete search history.

(56) References Cited

U.S. PATENT DOCUMENTS

| 5,417,694 A | 5/1995 | Marik |
| 5,762,125 A | 6/1998 | Mastrorio |
| 6,033,415 A | 3/2000 | Mittelstadt |
| 6,757,582 B2 | 6/2004 | Brisson et al. |

(Continued)

OTHER PUBLICATIONS

Cuppone M et al. "Design of Drill Guides for the Thoracic and Cervical Regions of the Spine." University of Leeds, May 2001.

(Continued)

*Primary Examiner* — Christopher Beccia
(74) *Attorney, Agent, or Firm* — Polsinelli PC

(57) ABSTRACT

An arthroplasty system for making resections in a patient knee. The system includes a femoral cutting guide having a patient specific mating region, and a distal planar surface distally spaced from a distal resection surface based on thicknesses of femoral and tibial implants. The distal planar surface may be used to check ligament balance. The system further includes a tibial cutting guide having a patient specific mating region and an anchor pin hole intersecting with a proximal resection slot near a medial or lateral edge of the proximal resection slot. The anchor pin hole being configured to receive an anchor pin that may serve as a sawing stop during a proximal resection.

20 Claims, 19 Drawing Sheets
(16 of 19 Drawing Sheet(s) Filed in Color)

(56) References Cited

U.S. PATENT DOCUMENTS

| | | |
|---|---|---|
| 9,402,637 B2 * | 8/2016 | Song .................. A61B 17/1764 |
| 9,814,475 B2 * | 11/2017 | Song .................. A61B 17/1764 |
| 2007/0038223 A1 | 2/2007 | Marquart |
| 2007/0066917 A1 | 3/2007 | Hodorek |
| 2008/0132783 A1 | 6/2008 | Revie et al. |
| 2014/0094694 A1 | 4/2014 | Moctezuma de la Barrera |
| 2014/0276870 A1 | 9/2014 | Eash |

OTHER PUBLICATIONS

MSOE Rapid Prototyping Center, Sterolithography (2001).
Notice of Allowance, U.S. Appl. No. 15/178,065, dated Jan. 12, 2018.
Response to Restriction, U.S. Appl. No. 15/178,065, dated Sep. 27, 2017.
Restriction Requirement, U.S. Appl. No. 15/178,065, dated Jul. 31, 2017.

* cited by examiner

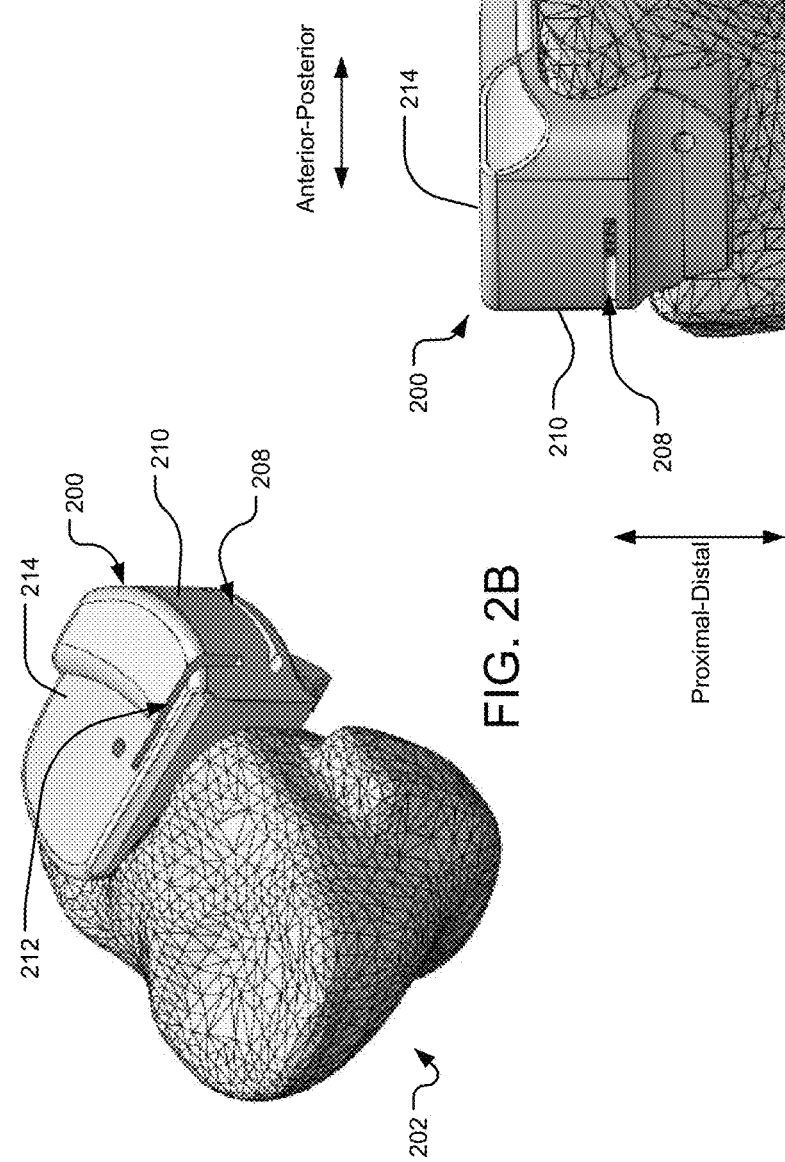
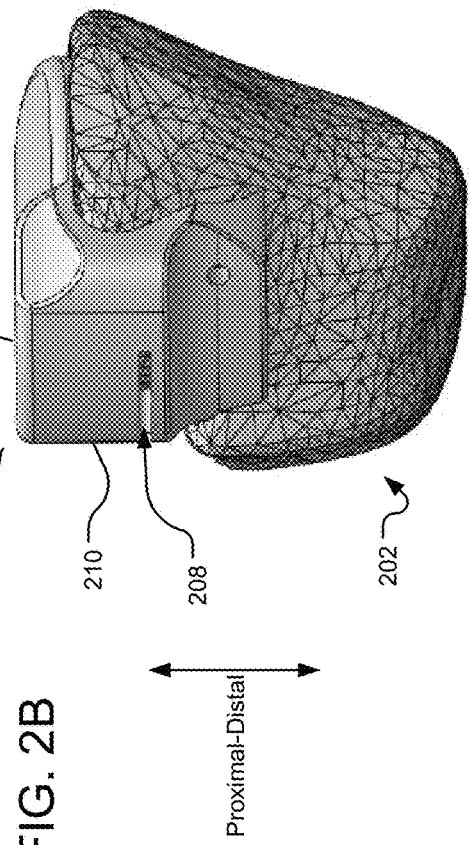

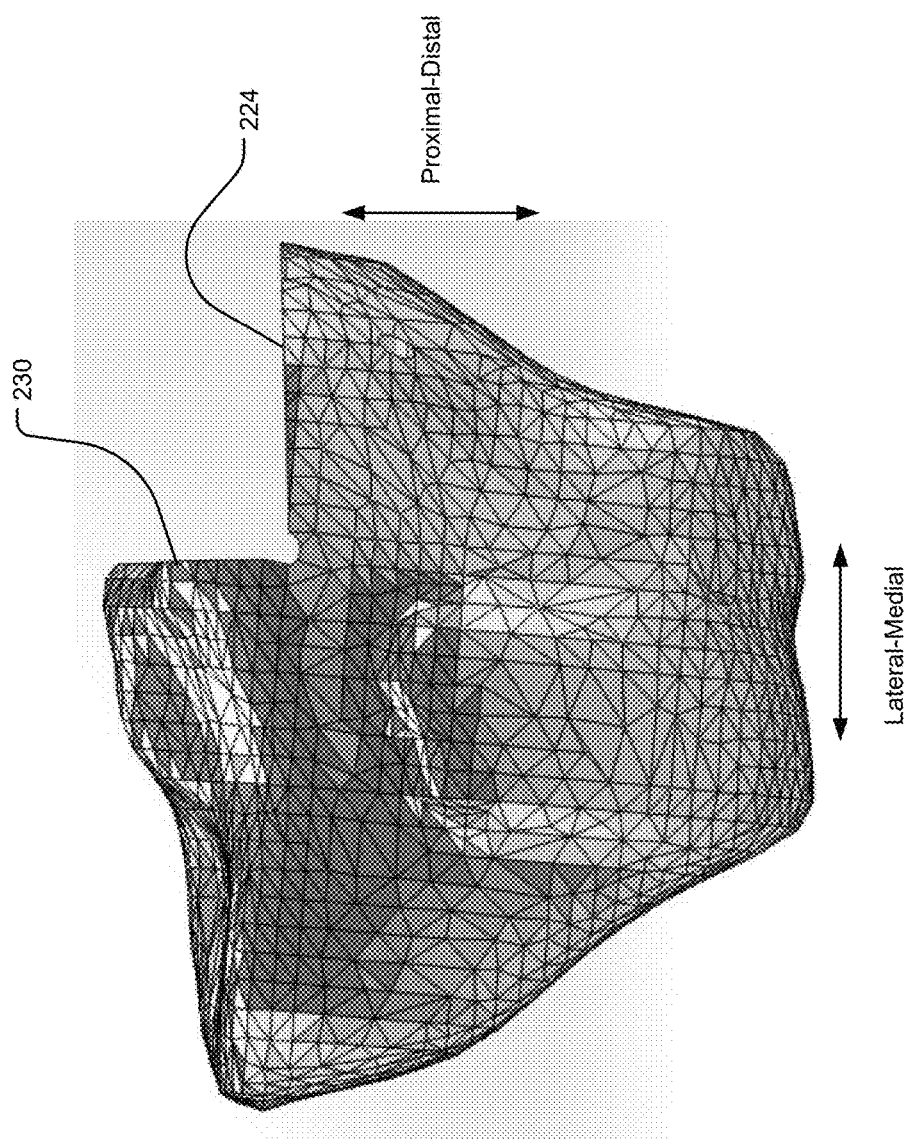

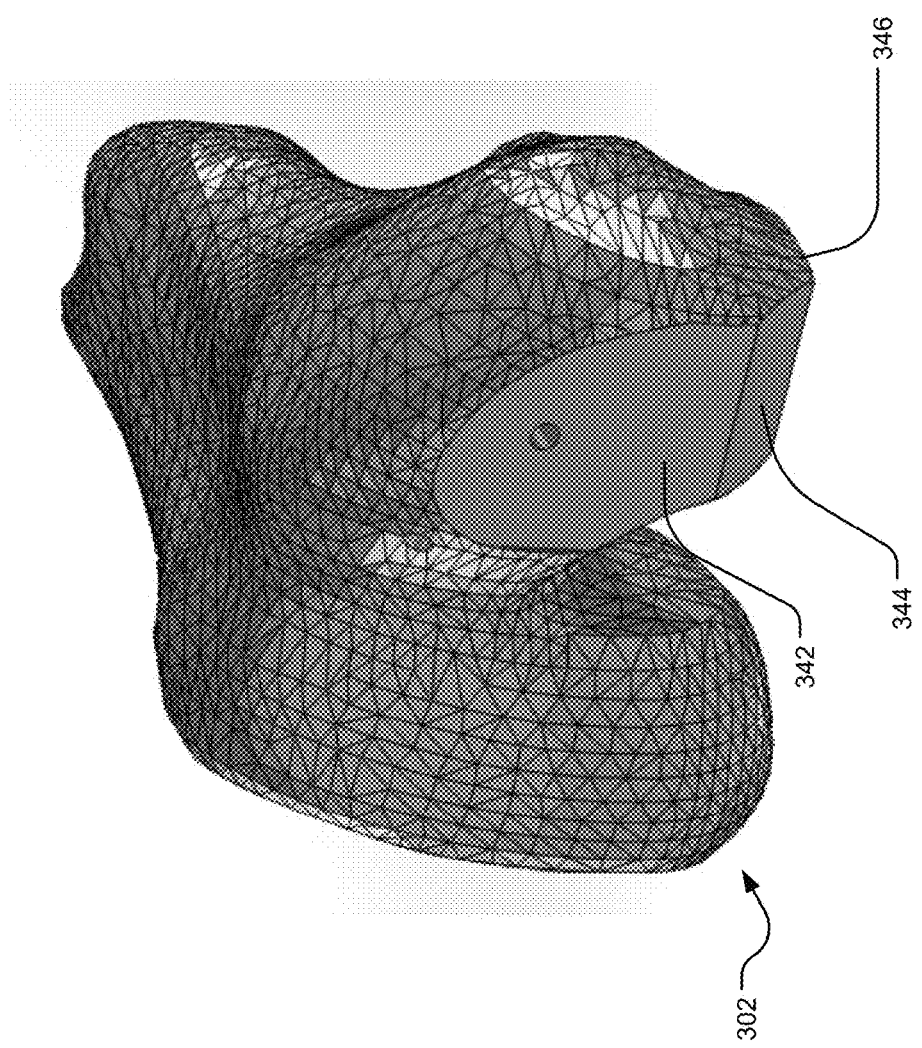

CUSTOMIZED ARTHROPLASTY CUTTING GUIDES AND SURGICAL METHODS USING THE SAME

CROSS REFERENCE TO RELATED APPLICATIONS

The present application is a continuation application of U.S. application Ser. No. 15/195,639 filed Jun. 28, 2016, which application is a continuation of U.S. application Ser. No. 13/749,095 filed Jan. 24, 2013, now U.S. Pat. No. 9,402,637, which application claims priority under 35 U.S.C. § 119 to U.S. provisional patent application 61/712,577, which was filed Oct. 11, 2012, entitled "PKR Cutting Guide." The above-referenced applications are hereby incorporated by reference in their entirety into the present application.

FIELD OF THE INVENTION

Aspects of the presently disclosed technology relate to medical apparatuses and methods. More specifically, the presently disclosed technology relates to unicompartmental customized arthroplasty cutting guides and surgical methods using such cutting guides.

BACKGROUND OF THE INVENTION

Over time and through repeated use, bones and joints can become damaged or worn. For example, repetitive strain on bones and joints (e.g., through athletic activity), traumatic events, and certain diseases (e.g., arthritis) can cause cartilage in joint areas, which normally provides a cushioning effect, to wear down. When the cartilage wears down, fluid can accumulate in the joint areas, resulting in pain, stiffness, and decreased mobility.

Arthroplasty procedures can be used to repair damaged joints. During a typical arthroplasty procedure, an arthritic or otherwise dysfunctional joint can be remodeled or realigned or an implant can be implanted into the damaged region. Arthroplasty procedures may take place in any of a number of different regions of the body, such as a knee, a hip, a shoulder, or an elbow.

One type of arthroplasty procedure is a total knee arthroplasty ("TKA"), in which a damaged knee joint is replaced with prosthetic implants. The knee joint may have been damaged by, for example, arthritis (e.g., severe osteoarthritis or degenerative arthritis), trauma, or a rare destructive joint disease. Typically, a candidate for a TKA has significant wear or damage in tow or more "compartments" of the knee. The knee is generally divided into three "compartments, including: medial (the inside part of the knee), lateral (the outside part of the knee), and the patellofemoral (the joint between the knee cap and the thighbone). During a TKA procedure, a damaged portion in the distal region of the femur may be removed and replaced with a metal shell, and a damaged portion in the proximal region of the tibia may be removed and replaced with a channeled piece of plastic having a metal stem. In some TKA procedures, a plastic button may also be added under the surface of the patella, depending on the condition of the patella.

Another type of arthroplasty procedure is a unicompartmental (knee) arthroplasty or a partial knee replacement ("UKA") in which only a portion (or a single compartment) of the knee is removed and replaced with prosthetic implants. Typically, a candidate for a UKA has significant wear or damage confined to primarily one compartment of the knee. A UKA may be a less invasive approach than a TKA and may have a quicker recovery time. A UKA may be utilized to prevent the spread of disease, such as in the early stages of osteoarthritis where the disease has only affected a portion of the knee and it is desirable to prevent the disease from spreading to other portions of the knee.

Implants that are implanted into a damaged region may provide support and structure to the damaged region and may help to restore the damaged region, thereby enhancing its functionality. Prior to implantation of an implant in a damaged region, the damaged region is prepared to receive the implant. For example, in a knee arthroplasty procedure, one or more of the bones in the knee area, such as the femur and/or the tibia, may be treated (e.g., cut, drilled, reamed, and/or resurfaced) to provide one or more surfaces that can align with the implant and thereby accommodate the implant.

Accuracy in implant alignment is an important factor to the success of a TKA or UKA procedure. A one to two millimeter translational misalignment may result in imbalanced ligaments and thus may significantly affect the outcome of the procedure. For example, implant misalignment may result in intolerable post-surgery pain and also may prevent the patient from having full leg extension and stable leg flexion.

To achieve accurate implant alignment, prior to treating (e.g., cut, drilled, reamed, and/or resurfaced) any regions of a bone, it is important to correctly determine the location at which the treatment will take place and how the treatment will be oriented. In some methods, an arthroplasty jig may be used to position and orient a resection or sawing instrument, such as a cutting, drilling, reaming, or resurfacing instrument on the regions of the bone. The arthroplasty jig may, for example, include one or more apertures and/or slots that are configured to accept such an instrument. However, under some methods, it is difficult to determine the proper orientation of an arthroplasty jig and more specifically, of a unicompartmental arthroplasty jig. Some methods utilize customized arthroplasty jigs to provide orientation of the treatment relative to the regions of the bone. However, such jigs often rely on a human to subjectively determine or "eyeball" rotational angles and the extent of the treatment. For example, when performing a resection in a knee region of a patient femur and/or tibia, many jigs rely on a surgeon to determine the proper orientation of the jig as well as how much of the bone to remove. In other words, once a surgeon has begun cutting to perform a resection, it is often difficult to accurately stop the cut.

Accordingly, there is a need in the art for customized arthroplasty cutting guides and surgical methods of using such cutting guides that increases the accuracy of arthroplasty procedures.

BRIEF SUMMARY OF THE INVENTION

Implementations described and claimed herein address the foregoing problems by providing an arthroplasty cutting guide for making resections in a knee region of a patient femur in preparing a patient knee for the implantation of a femoral implant and a tibial implant.

The knee region includes surface topography including surface contours of a femoral condylar surface and a trochlear groove surface. In one implementation, the femoral implant includes: an articular condylar surface; a femur contacting side opposite the articular condylar surface and including a distal resection contacting surface, a posterior resection contacting surface, and a chamfer resection contacting surface. The femoral implant has a first distal-proximal thickness extending perpendicular from the distal resection contacting surface to the articular condylar surface. In one implementation, the tibial implant includes an articular plateau surface and a tibia contacting side, which includes a proximal resection contacting surface, opposite the articular plateau surface. The tibial implant includes a second distal-proximal thickness extending perpendicular from the proximal resection contacting surface to the articular plateau surface.

In one implementation, the arthroplasty cutting guide comprises: a patient specific mating region, a distal resection slot, and a distal planar surface. The patient specific mating region is custom configured to interdigitate with the topography of the knee region and comprises surface contours that are a general negative image of the surface contours of the femoral condylar surface and the surface contours of the trochlear groove. The distal resection slot is configured to guide a distal resection in the knee region when the patient specific mating region interdigitates with the topography of the knee region such that the surface contours of the mating region make corresponding surface contact with the surface contours of the femoral condylar surface and the trochlear groove. The distal planar surface is parallel to the distal resection slot and is distally spaced apart from the distal resection surface by a distance equal to the sum of the first distal-proximal thickness of the femoral implant and the second distal-proximal thickness of the tibial implant.

Other implementations described and claimed herein provide an arthroplasty system for making resections in a knee region of a patient tibia in preparing a patient knee for the implantation of a tibial implant. The knee region includes surface topography including surface contours of a tibial plateau surface. In one implementation, the arthroplasty system comprises a cutting guide and an anchor pin.

The cutting guide comprises a patient specific mating region, a proximal resection slot, and an anchor pin hole. The patient specific mating region is custom configured to interdigitate with the topography of the knee region and comprises surface contours that are a general negative image of the surface contours of the tibial plateau surface. The proximal resection slot comprises an exterior opening defined in an exterior anterior surface of the cutting guide. The proximal resection slot extends anterior-posterior and medial-lateral in the cutting guide and is configured to guide a proximal resection in the knee region when the patient specific mating region interdigitates with the topography of the knee region such that the surface contours of the mating region make corresponding surface contact with the surface contours of the tibial plateau surface. The anchor pin hole comprises an exterior opening defined in the exterior anterior surface of the cutting guide. The anchor pin hole extends generally anterior-posterior through the cutting guide and intersects the proximal resection slot near a medial or lateral edge of the proximal resection slot. The anchor pin comprises an elongated shaft configured to be received in the anchor pin hole in securing the cutting guide to the patient tibia.

Other implementations described and claimed herein provide methods of performing a knee arthroplasty. In one implementation, a tibia cutting guide is placed a tibial plateau of a patient tibia. The tibia cutting guide includes a patient specific mating region, a proximal resection slot, and an anchor pin hole. The patient specific mating region is custom configured to interdigitate with a topography of the tibial plateau and comprises surface contours that are a general negative image of surface contours of the tibial plateau. The proximal resection slot comprises an exterior opening defined in an exterior anterior surface of the cutting guide, and the proximal resection slot extends anterior-posterior and medial-lateral in the cutting guide. The anchor pin hole comprises an exterior opening defined in the exterior anterior surface of the cutting guide, and the anchor pin hole extends generally anterior-posterior through the cutting guide, intersecting the proximal resection slot near a medial or lateral edge of the proximal resection slot. The patient specific mating region is caused to interdigitate with the topography of the tibial plateau. The anchor pin is inserted into the patient tibia via the anchor pin hole such that the anchor pin is present within both the anchor pin hole and the patient tibia. With the mating region interdigitated with the topography of the tibial plateau, a proximal resection of the patient tibia is made via the proximal resection slot.

In another implementation, a proximal resection is created a patient tibia near a tibial plateau of the patient tibia. A femoral cutting guide is placed on a condylar region of a patient femur. The femoral cutting guide includes a patient specific mating region, a distal resection slot, and a distal planar surface. The patient specific mating region is custom configured to interdigitate with a topography of the condylar region and comprises surface contours that are a general negative image of surface contours of the condylar region. The distal resection slot comprises an exterior opening defined in an exterior anterior surface of the cutting guide, and the distal resection slot extends anterior-posterior and medial-lateral in the cutting guide. The distal planar surface is parallel to the distal resection slot and distally spaced apart from the distal resection surface. The patient specific mating region is caused to interdigitate with the topography of the condylar region. With the patient specific mating region interdigitated with the topography of the condylar region, the distal planar surface is caused to abut against the proximal resection.

Other implementations are also described and recited herein. Further, while multiple implementations are disclosed, still other implementations of the presently disclosed technology will become apparent to those skilled in the art from the following detailed description, which shows and describes illustrative implementations of the presently disclosed technology. As will be realized, the presently disclosed technology is capable of modifications in various aspects, all without departing from the spirit and scope of the presently disclosed technology. Accordingly, the drawings and detailed description are to be regarded as illustrative in nature and not limiting.

BRIEF DESCRIPTION OF THE DRAWINGS

The patent application file contains at least one drawing executed in color. Copies of this patent or patent application publication with color drawing(s) will be provided by the Office upon request and payment of necessary fee.

FIGS. 2B and 2C show the tibia cutting guide and the tibia of FIG. 2A with the tibia cutting guide interdigitated with the tibia.

FIG. 6 depicts an anterior elevation view of the tibia of FIG. 5 with the anchor pin removed.

FIG. 11 shows a distal resection, a posterior resection, and a chamfer resection of the femur.

DETAILED DESCRIPTION

Aspects of the presently disclosed technology involve customized unicompartmental arthroplasty cutting guides and methods of using the same during arthroplasty procedures. In one aspect, the cutting guides are customized to fit specific bone surfaces of a joint (e.g., knee, elbow, ankle, wrist, hip, shoulder, skull/vertebrae, vertebrae/vertebrae interface, etc.) of a specific patient to treat (e.g., cut, drilled, reamed, and/or resurfaced) the bone to provide one or more surfaces that can align with an implant and thereby accommodate the implant. In some aspects, depending on the implementation, both the implant and the cutting guide are automatically planned and generated according to the systems, apparatuses, and methods similar to those disclosed in U.S. patent application Ser. No. 12/636,939 to Park et al., entitled "Unicompartmental Customized Arthroplasty Cutting Jigs and Methods of Making the Same and filed on Dec. 14, 2009, which is incorporated by reference in its entirety into this Detailed Description.

Figure 1:
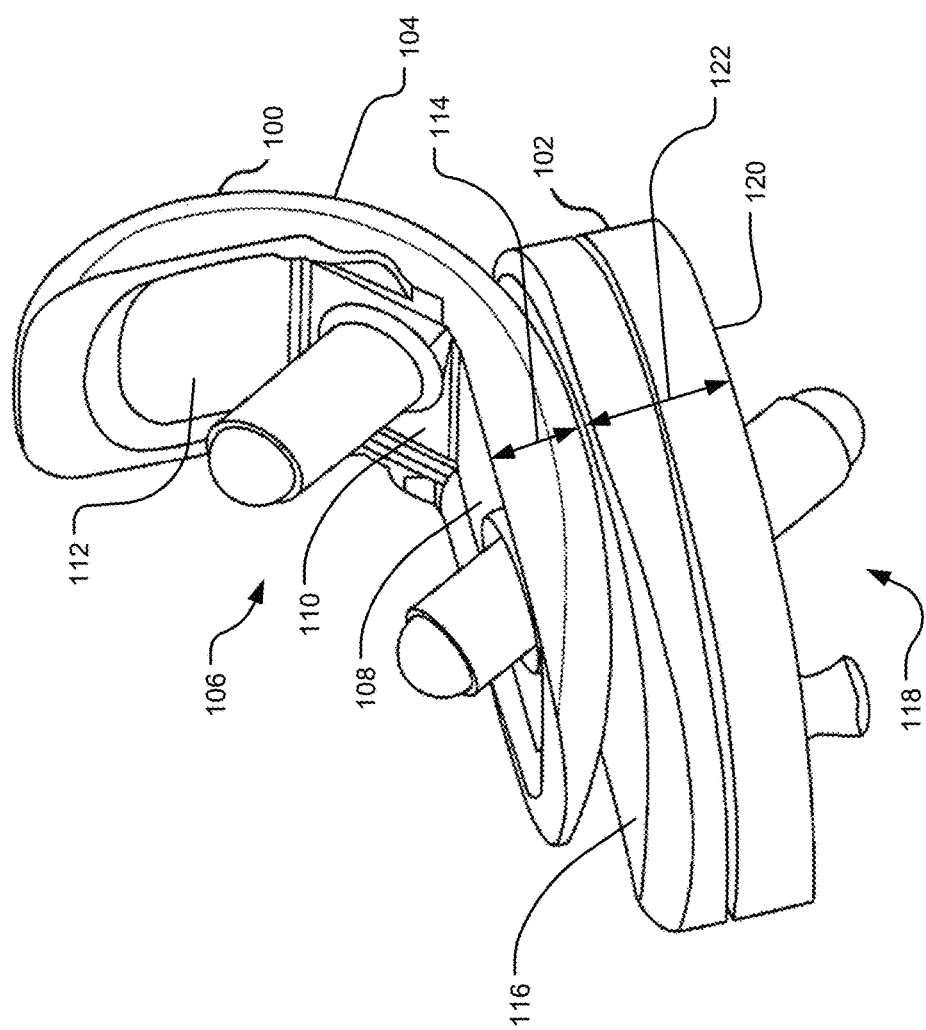
FIG. 1 is an isometric view of femoral and tibial unicompartmental implants interfaced with each other.

For an overview discussion of the implants for which bone surfaces in a knee area are treated to align with and accommodate, reference is made to FIG. 1, which illustrates an isometric view of a femoral unicompartmental implant 100 interfaced with a tibial unicompartmental implant 102.

In one implementation, the femoral implant 100 includes an articular condylar surface 104 and a femur contacting side 106 opposite the articular condylar surface 104. The femur contacting side 106 includes one or more surfaces each adapted to contact or otherwise engage a bone surface in a patient femur. In one implementation, the femur contacting side 106 includes a distal resection contacting surface 108, a chamfer resection contacting surface 110, and a posterior resection contacting surface 112, which are adapted to engage a distal resection, chamfer resection, and a posterior resection in the patient femur that are made using a femoral cutting guide as described herein. The femoral implant 100 includes a distal-proximal thickness 114 extending perpendicular from the distal resection contacting surface 108 to the articular condylar surface 104.

Similarly, in one implementation, the tibial implant 102 includes an articular plateau surface 116 and a tibia contacting side 118. The tibia contacting side 118 includes one or more surfaces, each of which is adapted to contact or otherwise engage a bone surface in a patient tibia. In one implementation, the tibia contacting side 118 includes a proximal resection contacting surface 120, which is adapted to engage a proximal resection in the patient tibia that is made using a tibial cutting guide as described herein. The tibial implant 102 includes a distal-proximal thickness 122 extending perpendicular from the proximal resection contacting surface 120 to the articular plateau surface 116.

Prior to implantation of the femoral implant 100 or the tibial implant 102, the damaged region in the femur or the tibia, respectively, is prepared to receive the implant. Stated differently, the femur or the tibia is treated (e.g., cut, drilled, reamed, and/or resurfaced) using an arthroplasty cutting guide to provide one or more resections that can align and mate with corresponding surfaces of the implant 100 or 102 and thereby accommodate the implant 100 or 102.

Figure 2A:
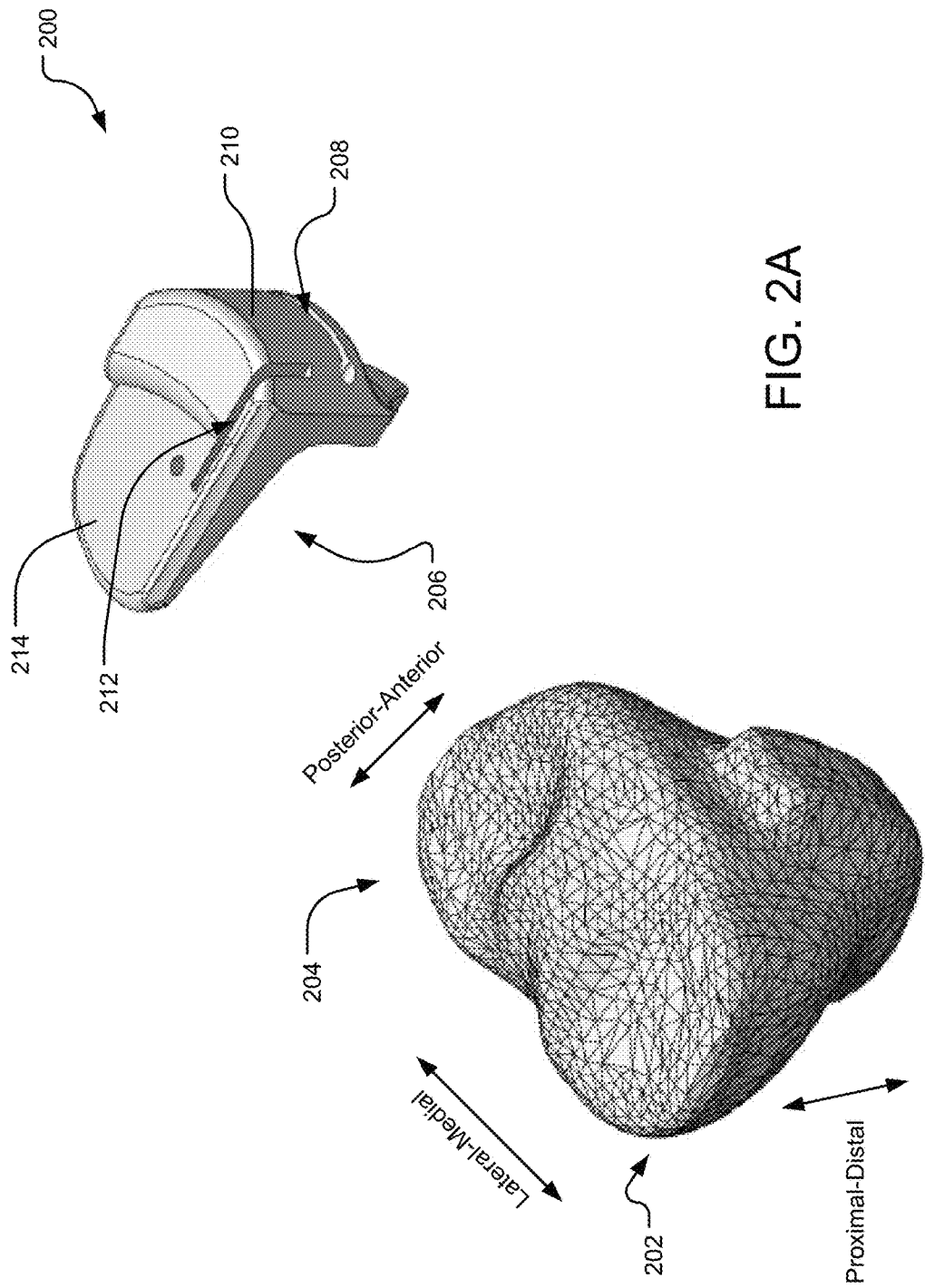
FIG. 2A illustrates an example tibia cutting guide and proximal tibia plateau.

For a detailed discussion of an arthroplasty system for making resections in a knee region to prepare a patient knee for the implantation of the tibial implant 102, reference is made to FIG. 2A, which shows a tibia cutting guide 200 and a patient tibia 202 in the patient knee. As can be understood from FIG. 2A, the patient tibia 202 includes a surface topology including surface contours of a tibial plateau surface 204.

In one implementation, the tibia cutting guide 200 is custom generated to allow a surgeon to accurately and quickly perform an arthroplasty procedure. In other words, the tibia cutting guide 200 includes a patient specific mating region 206 configured to interdigitate with the topography of the knee region. The patient specific mating region 206 includes surface contours that are a general negative image of the surface contours of the tibial plateau surface 204.

The tibia cutting guide 200 includes a proximal resection slot 208 defined in an exterior anterior surface 210 and a vertical resection slot 212 defined in an exterior proximal surface 214. The proximal resection slot 208 is configured to guide a proximal resection in the tibia 202, and the vertical resection slot 212 is configured to guide at least a beginning of a vertical (i.e., distal-proximal) resection in the tibia 202.

As can be understood from FIGS. 2B and 2C, when the tibia cutting guide 200 is used during an arthroplasty procedure, the patient specific mating region 206 interdigitates with the topography of the knee region such that the surface contours of the patient specific mating region 206 make corresponding surface contact with the surface contours of the tibial plateau surface 204. As such, when the surface topography of the knee region is received into the patient specific mating region 206, the surfaces 204 and 206 matingly match, thereby increasing stability during and accuracy of the arthroplasty procedure.

Figure 3A:
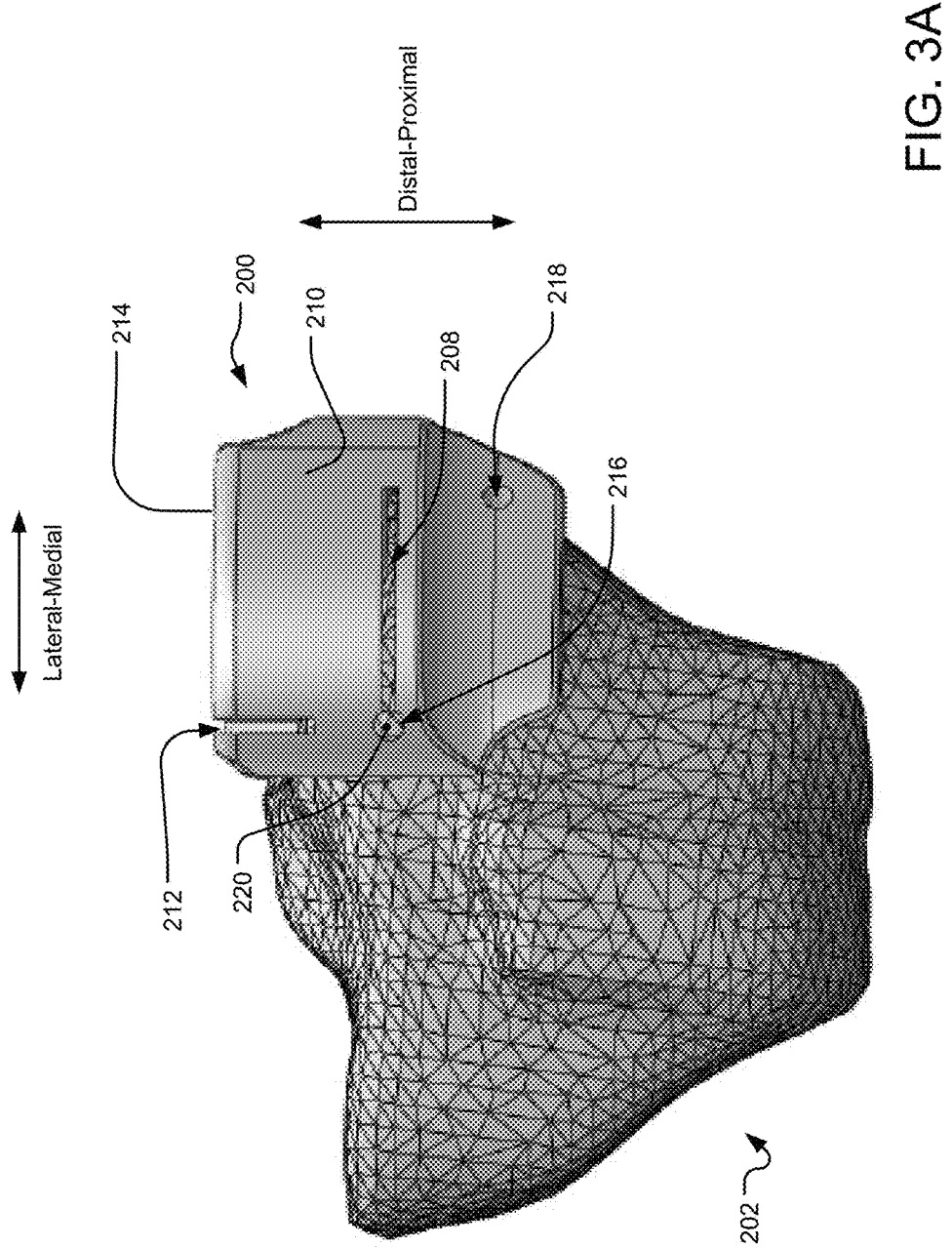
FIGS. 3A and 3B show side and top views, respectively, of the interdigitated tibia cutting guide of FIG. 2A.
Figure 3B:
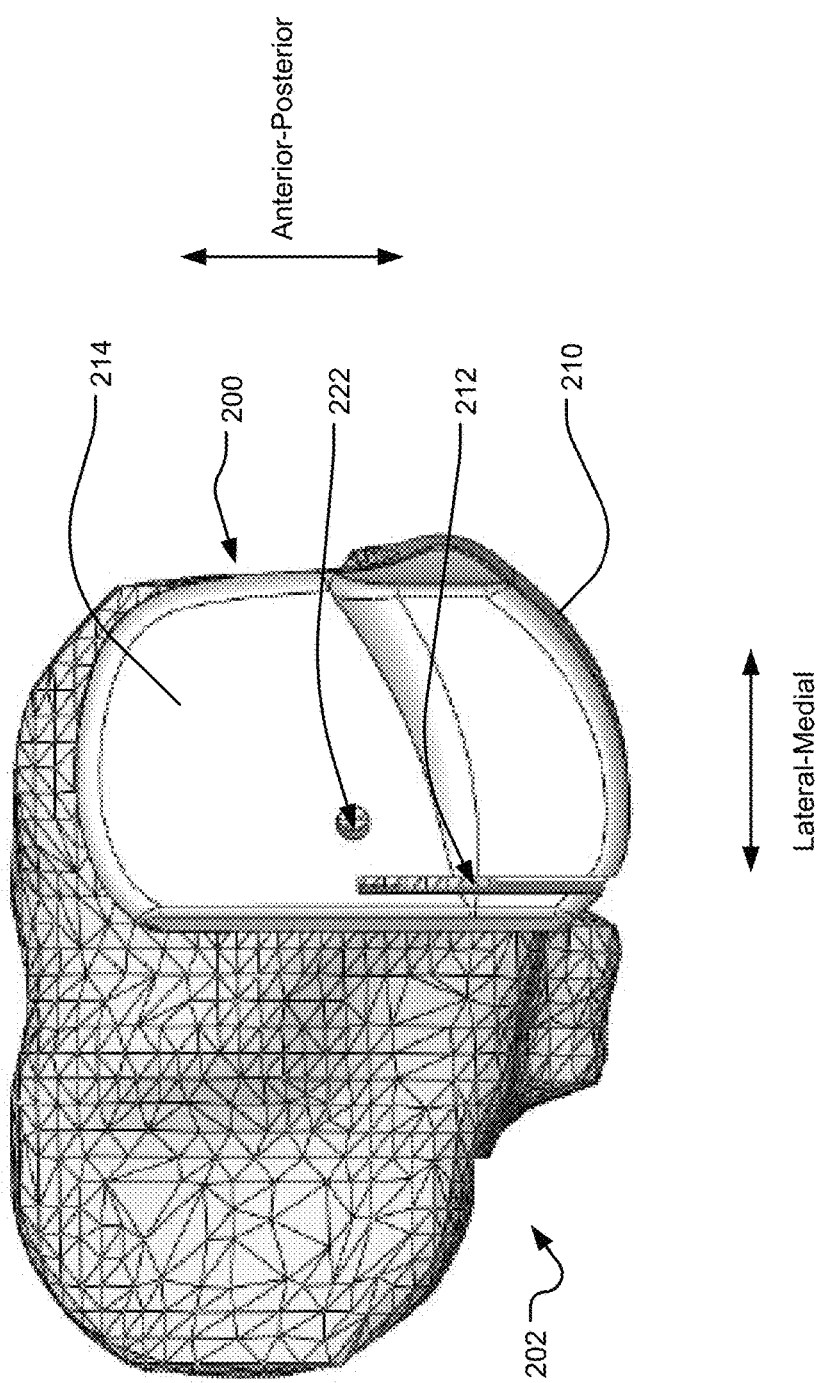

Turning to FIGS. 3A and 3B, which are side and top views, respectively, of the tibia cutting guide 200 interdigitated with the tibia 202, it will be understood that in one implementation, the proximal resection slot 208 is an exterior opening extending anterior-posterior and medial-lateral in the tibia cutting guide 200, and the vertical resection slot 212 is an exterior opening extending anterior-posterior and distal-proximal in the tibia cutting guide 200. The exterior openings are adapted to receive and guide a resection or sawing instrument to perform proximal and vertical resections of the tibia 202.

The tibia cutting guide 200 is configured to assist a surgeon during the performance of such resections by increasing, for example, accuracy and stability. To achieve this, in one implementation, the tibia cutting guide 200 includes one or more anchor pin holes 216, 218, and 222 including exterior openings that are adapted to receive an elongated shaft of an anchor pin 228 (shown in FIG. 4) in an interference fit (e.g., using friction) to secure the tibia cutting guide 200 to the patient tibia 202. When the anchor pin 228 is inserted into the patient tibia 202 via one of the anchor pin holes 216, 218, or 222, the anchor pin 228 is present in both the anchor pin hole 216, 218, or 222 and the patient tibia 202. In one implementation, the anchor pin holes include an anterior pin hole 216 defined in the exterior anterior surface 210, a medial/lateral pin hole 218 defined in the exterior anterior surface 210, and a proximal pin hole 222 defined in the exterior proximal surface 214.

The anterior pin hole 216 extends generally anterior-posterior through the tibia cutting guide 200. As shown in the example in FIGS. 3A and 3B, the anterior pin hole 216 may be substantially coplanar with the proximal resection slot 208 and/or the vertical resection slot 212. The anterior pin hole 216 includes a longitudinal center axis 220 positioned at the general center of the exterior opening of the anterior pin hole 216. In one implementation, the longitudinal center axis 220 is substantially centered distal-proximal relative to a distal-proximal thickness of the proximal resection slot 208 and medial-lateral relative to a medial-lateral thickness of the vertical resection slot 212.

The characteristics of the proximal resection slot 208 and the anterior pin hole 216 are configured to assist a surgeon during the performance of proximal resections. In one implementation, the anterior pin hole 216 intersects with the proximal resection slot 208 near a medial or lateral edge of the proximal resection slot 208 such that the anterior pin hole 216 defines the medial or lateral edge of the proximal resection slot 208. When the proximal resection is performed, the surgeon begins the proximal resection until the anchor pin in the proximal pin hole 222 is reached, which is removed to complete the proximal resection. At the end of the proximal resection, the anchor pin 228 in the anterior pin hole 216 serves as a sawing stop to prevent the surgeon from cutting too far into the tibia 202. As such, the anchor pin 228 is made from a material that is harder and more saw resistant than a material of the tibia cutting guide 200 around a border of the proximal resection slot 208. For example, the anchor pin 228 may be made from a metal or ceramic, and the material bordering the proximal resection slot in the tibia cutting guide 200 may be made from a polymer.

In some implementations, the anchor pin 228 in the anterior pin hole 216 may serve as a sawing stop during a vertical resection while the tibia cutting guide 200 is interdigitated with the topography of the tibial plateau surface 204. In other implementations, the anterior pin hole 216 and the vertical resection slot 212 do not intersect. Accordingly, at least a beginning of the vertical resection is performed using the vertical resection slot 212. In other words, a vertical resection line is scored using the vertical resection slot 212.

Figure 4:
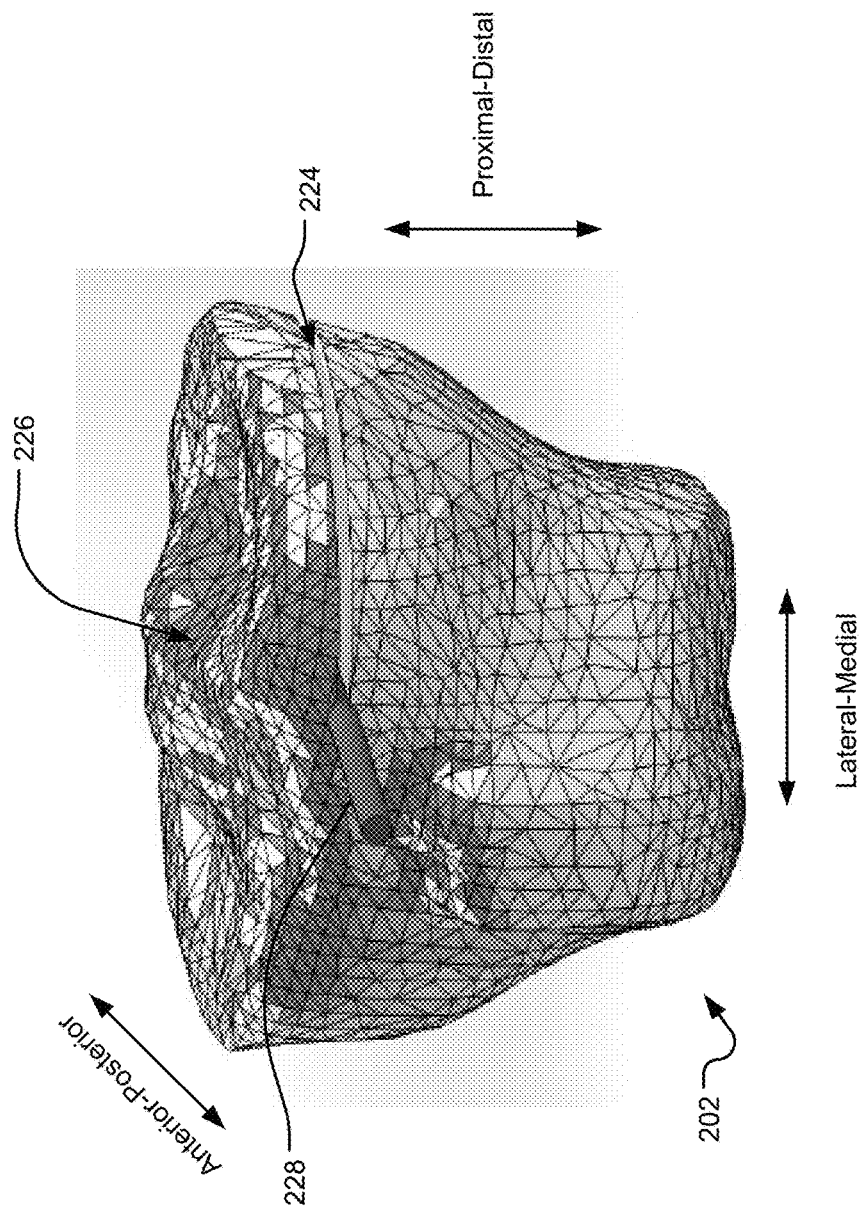
FIG. 4 illustrates a proximal resection of and a vertical score in the tibia with an anchor pin inserted.
Figure 5:
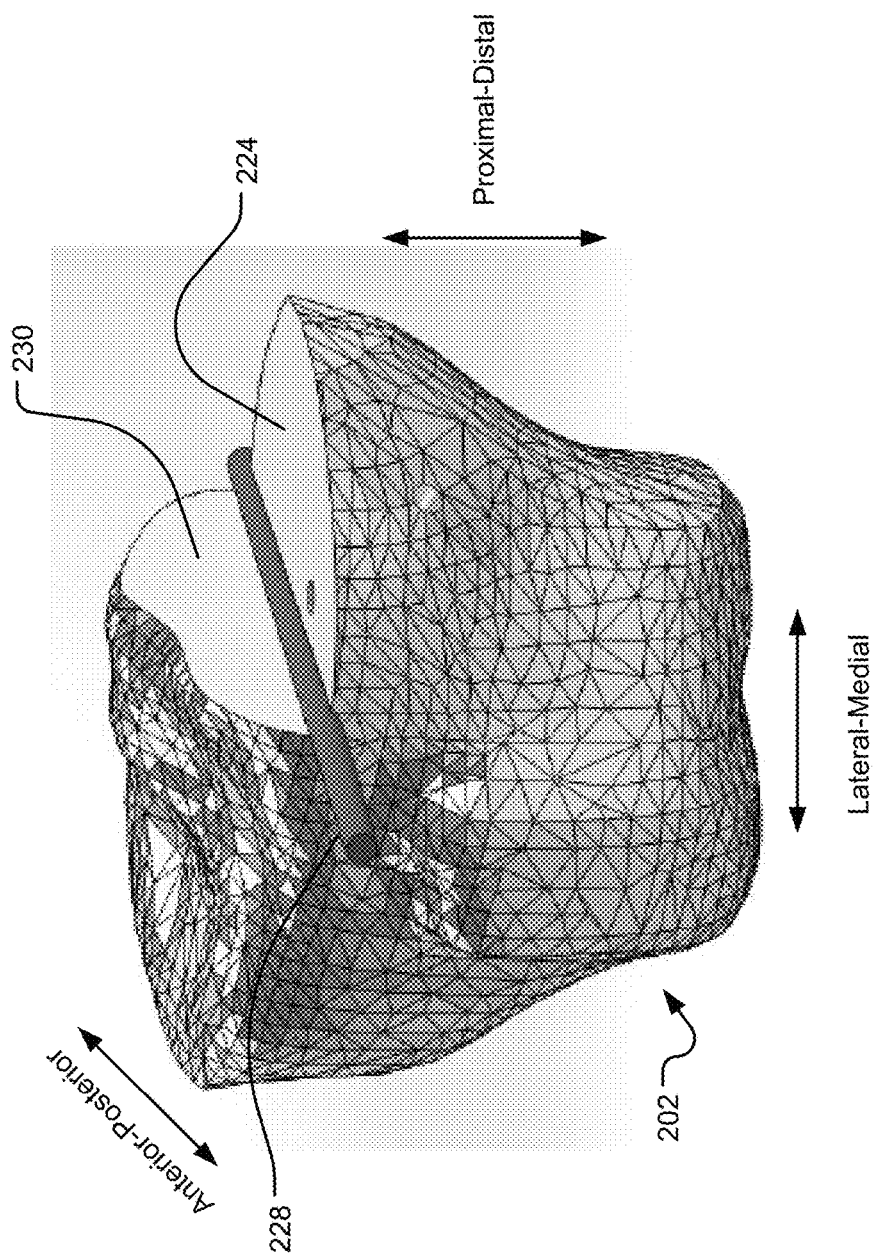
FIG. 5 is the same view as FIG. 4 with the vertical resection of the tibia completed.

Turning to FIG. 4, after making the proximal resection 224 and scoring the vertical resection line 226, the anchor pin 228 and the tibia cutting guide 200 may be removed from the tibia 202. The anchor pin 228 is then reinserted into a hole in the patient tibia that was formerly occupied by the anchor pin 228 when the anchor pin 228 was inserted through the anterior pin hole 216 into the patient tibia 202. As can be understood from FIG. 5, in one implementation, the vertical resection 230 is completed using the anchor pin 228 as a guide and sawing stop without the tibia cutting guide 200 being mounted on the patient tibia 202. Using the anchor pin 228 as a sawing stop for the proximal resection and/or the vertical resection, not only prevents the surgeon from cutting too far into the tibia 202, but stress risers that could otherwise cause a crack to propagate horizontally or vertically from a respective resection are substantially eliminated. As shown in FIG. 6, after the anchor pin 228 is removed, the proximal resection 224 and the vertical resection 230 are complete, and the tibia 202 is prepared to receive the tibial implant 102.

Figure 7A:
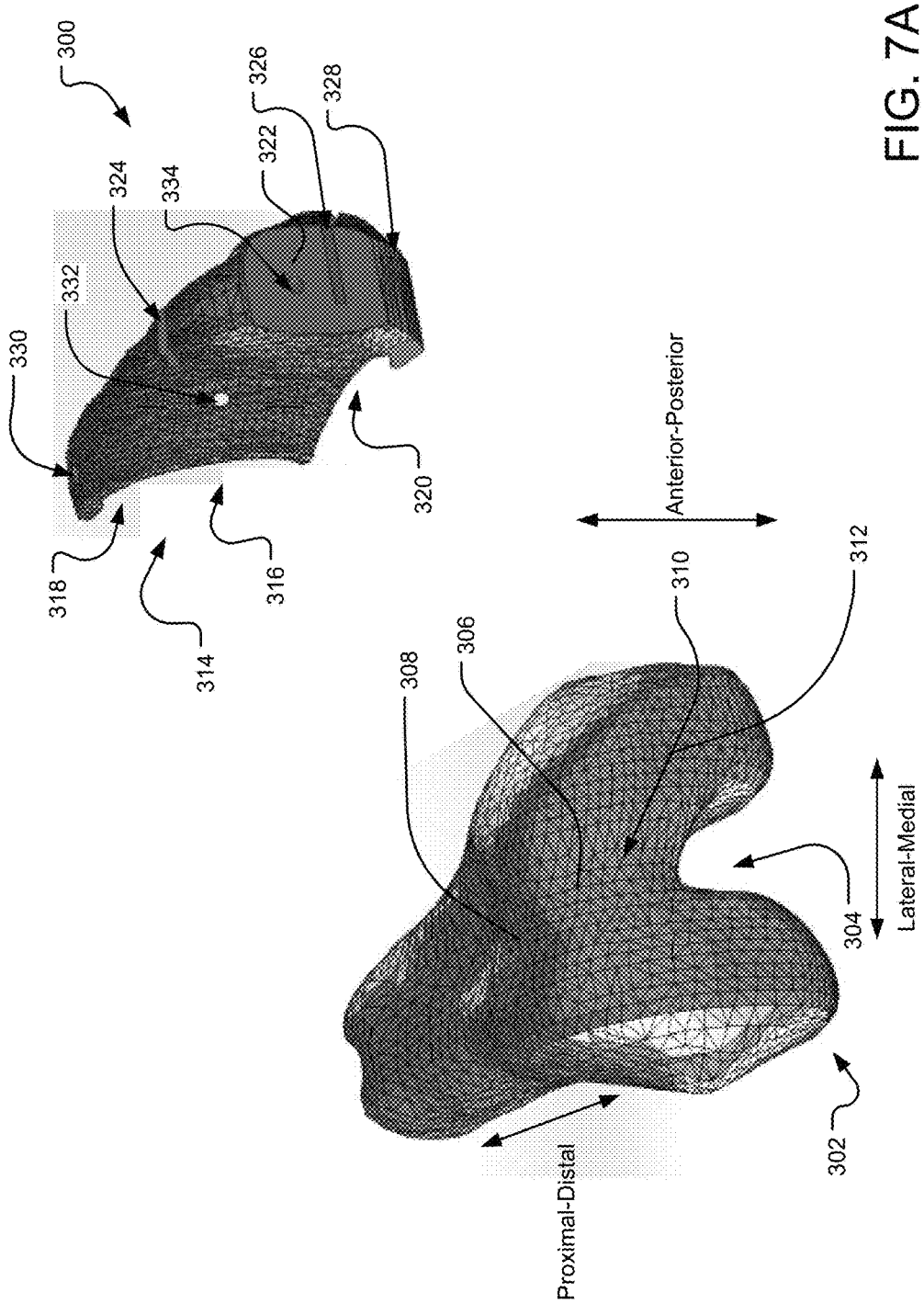
FIG. 7A shows an example femoral cutting guide and femur.

For a detailed discussion of an arthroplasty system for making resections in a knee region to prepare a patient knee for the implantation of the femoral implant 100, reference is made to FIG. 7A, which shows a femur cutting guide 300 and a patient femur 302 in the patient knee. The patient femur 302 includes a trochlear groove surface 304 having a distal trochlear groove 306 and an anterior trochlear groove 308. The patient femur 302 further includes a condylar surface 310 having a distal condyle 312. As can be understood from FIG. 7A, the femur 302 has a surface topography including surface contours of the condylar surface 310 and the trochlear groove surface 304.

The femur cutting guide 300 is custom generated to allow a surgeon to accurately and quickly perform an arthroplasty procedure. In other words, the femur cutting guide 300 includes a patient specific mating region 314 configured to interdigitate with the topography of the knee region. The patient specific mating region 314 includes surface contours that are a general negative image of the surface contours of the condylar surface 310 and the trochlear groove surface 304. In one implementation, the patient specific mating region 314 includes: a distal trochlear groove region 316 adapted to receive the distal trochlear groove 306; an anterior trochlear groove mating region 318 adapted to receive the anterior trochlear groove 308; and a distal condylar mating region 320 adapted to receive the distal condyle 312.

In one implementation, the femur cutting guide 300 includes a distal planar surface 322, a distal resection slot 324, a chamfer resection slot 326, a posterior resection slot 328, and one or more anchor pin holes 330, 332, and 334. The distal resection slot 324, the chamfer resection slot 326, and the posterior resection slot 328 are configured to guide a distal resection, chamfer resection, and posterior resection, respectively. In one implementation, the distal resection slot 324 is positioned generally parallel to the distal planar surface 322, and the chamfer resection slot 326 is defined in the distal planar surface 322. The posterior resection slot 328 is positioned generally perpendicular to the distal resection slot 324, and the chamfer resection slot 326 is positioned at angle (e.g., approximately 45 degrees) relative to the distal resection slot 324. In one implementation, the chamfer resection slot is further positioned at an angle (e.g., approximately 45 degrees) relative to the posterior resection slot 328. The angular relationship of the chamfer resection slot 326 to the distal resection slot 324 and/or the posterior resection slot 328 may be based on the geometry of the femoral implant 100, such as the distal resection contacting surface 108, the chamfer resection contacting surface 110, and the posterior resection contacting surface 112.

Figure 7B:
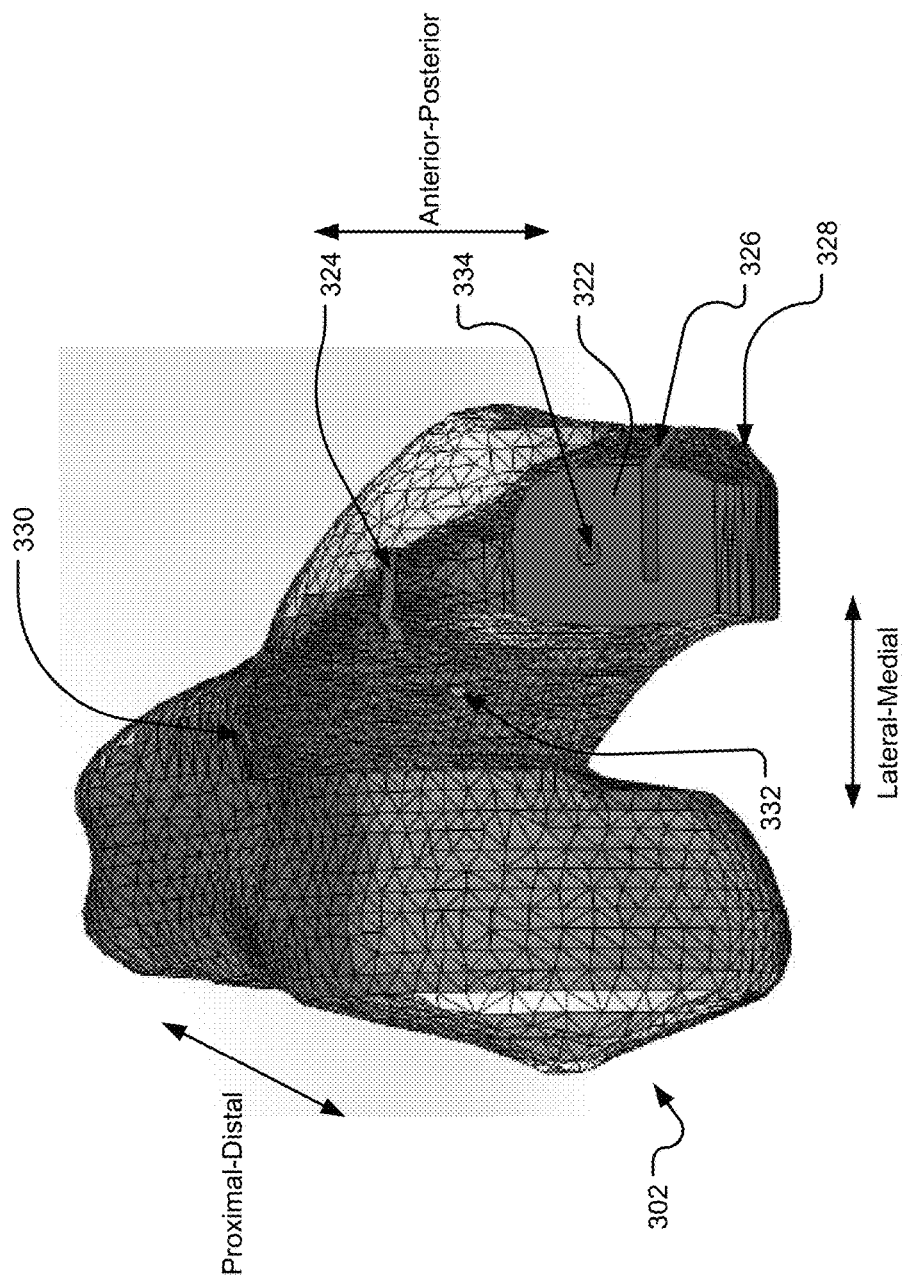
FIG. 7B illustrates the femoral cutting guide and the femur of FIG. 7A with the femoral cutting guide interdigitated with the femur.

As can be understood from FIG. 7B, when the femur cutting guide 300 is used during an arthroplasty procedure, the patient specific mating region 314 interdigitates with the topography of the knee region such that the surface contours of the patient specific mating region 314 make corresponding surface contact with the surface contours of the condylar surface 310 and the trochlear groove surface 304. As such, when the surface topography of the knee region is received into the patient specific mating region 314, the condylar surface 310 and the trochlear groove surface 304 matingly match with the patient specific mating region 314, thereby increasing stability during and accuracy of the arthroplasty procedure.

Figure 8:
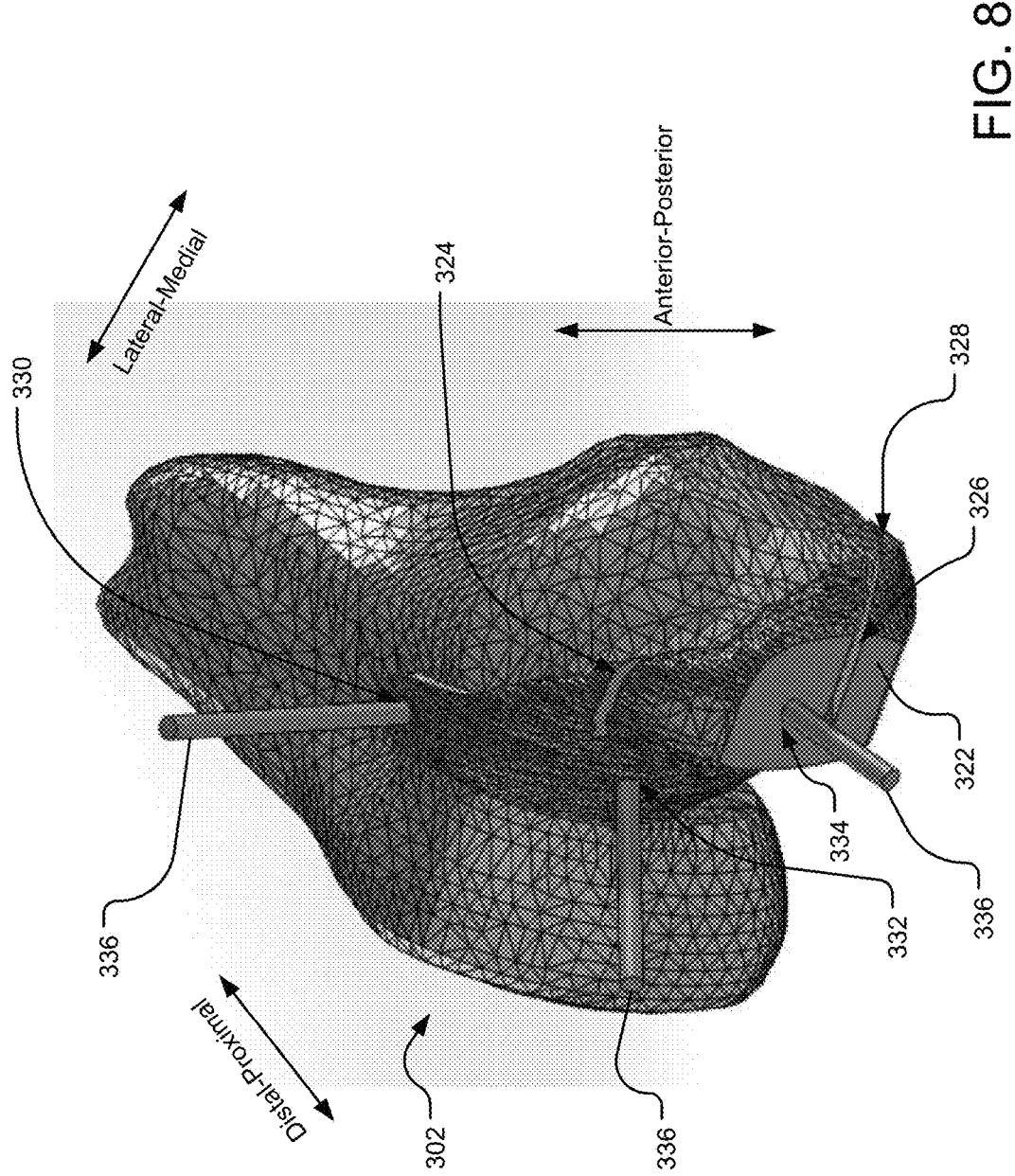
FIG. 8 shows a side perspective view of the interdigitated femoral cutting guide of FIG. 7B with anchor pins inserted.

Turning to FIG. 8, the femur cutting guide 300 is fixed into place on the patient femur 302 using anchor pins 336. In one implementation, one of the anchor pins 336 is inserted into the patient femur 302 via the first anchor pin hole 330, which extends through the anterior trochlear groove mating region 318 in a direction generally parallel to the distal resection slot 324. Another of the anchor pins 336 is inserted into the patient femur 302 via the second anchor pin hole 332, which extends through the distal trochlear mating region 316 in a direction angled relative the distal resection slot 324. Yet another of the anchor pins 336 is inserted into the patient femur 302 via the third anchor pin hole 334, which extends through the distal condylar mating region 320 in a direction generally perpendicular relative to the distal resection slot 324.

Figure 9:
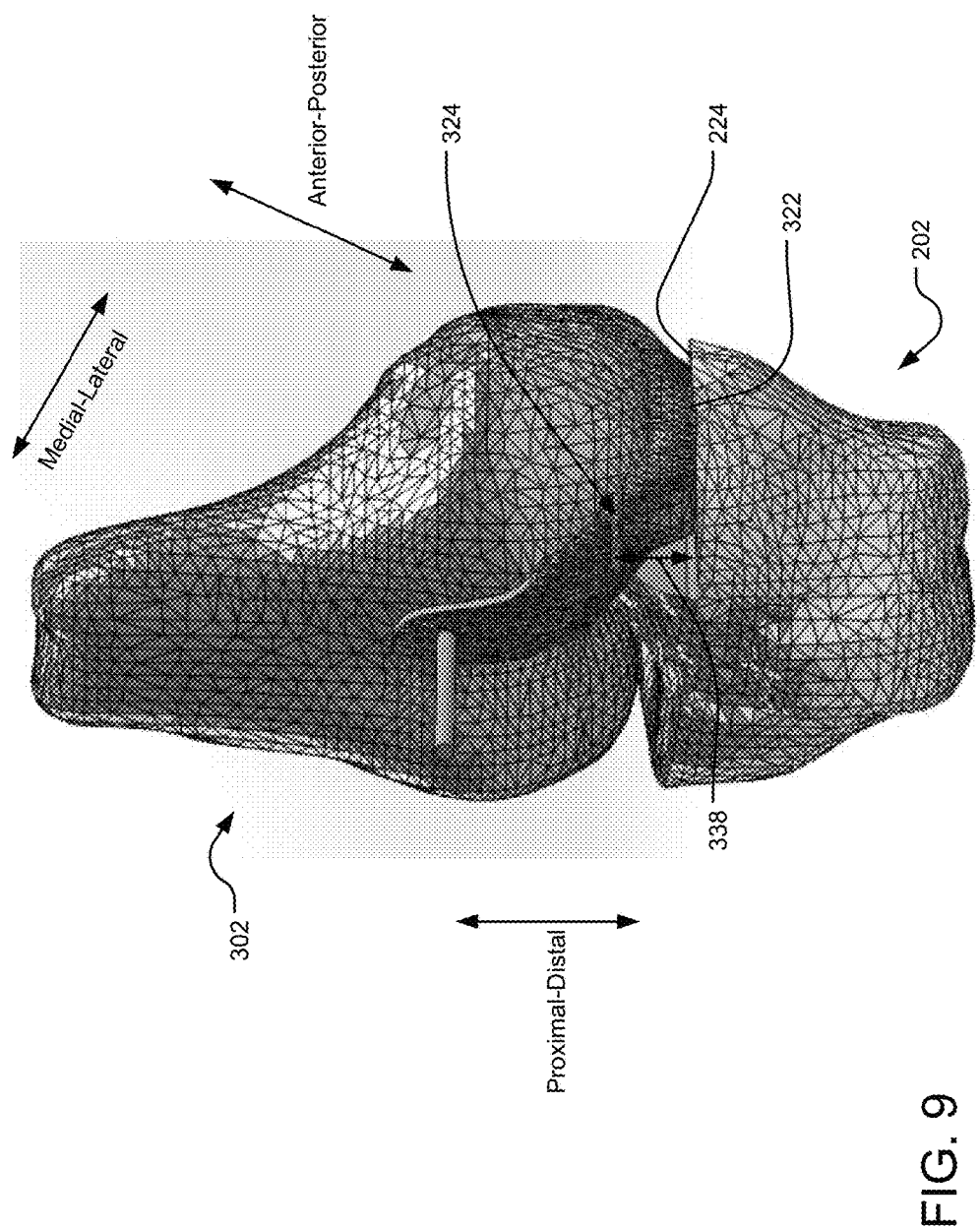
FIG. 9 illustrates a distal plane of the femoral cutting guide in planar contact with the proximal resection of the tibia.

As can be understood from FIG. 9, in one implementation, before performing the distal, chamfer, and/or posterior resections, ligament balance may be checked by placing the distal planar surface 322 in planar contact with the proximal resection 224 of the patient tibia 202. While the distal planar surface 322 is in such planar contact with the proximal resection 224, the femoral cutting guide 300 is engaged with the condylar surface 310 of the patient femur 302 and with the proximal resection 224 of the patient tibia 202. In one implementation, the distal planar surface 322 is distally spaced apart from the distal resection slot 324 by a distance 338 equal to a sum of the first and second distal-proximal thicknesses 114 and 122 of the femoral and tibial implants 100 and 102 (see FIG. 1). As such, by checking the ligament balance using the femur cutting guide 200, it may be verified that the ligament balance will be achieved with the implants 100 and 102.

Figure 10A:
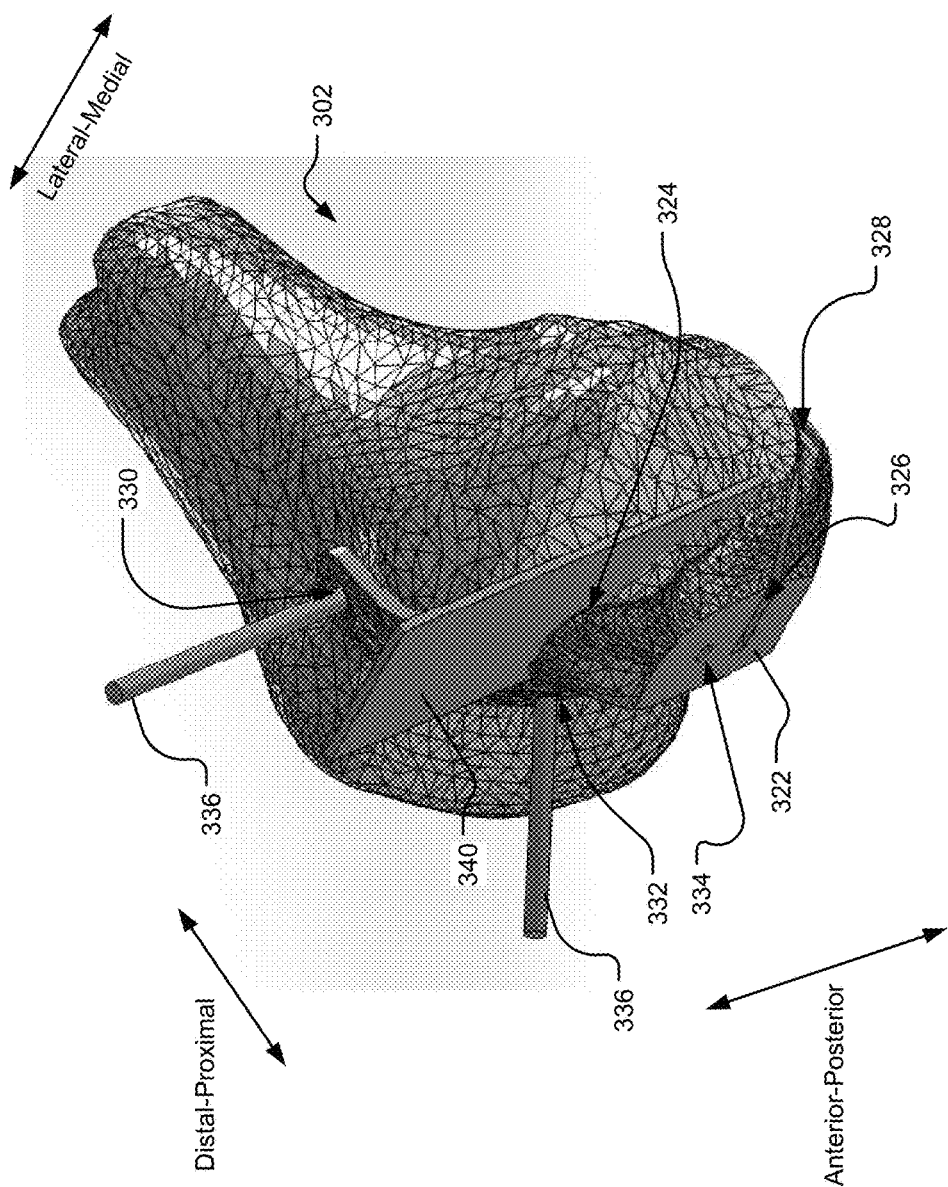
FIG. 10A shows a side perspective view of the interdigitated femoral cutting guide of FIG. 7B with a resection or sawing instrument inserted into a distal resection slot.
Figure 10B:
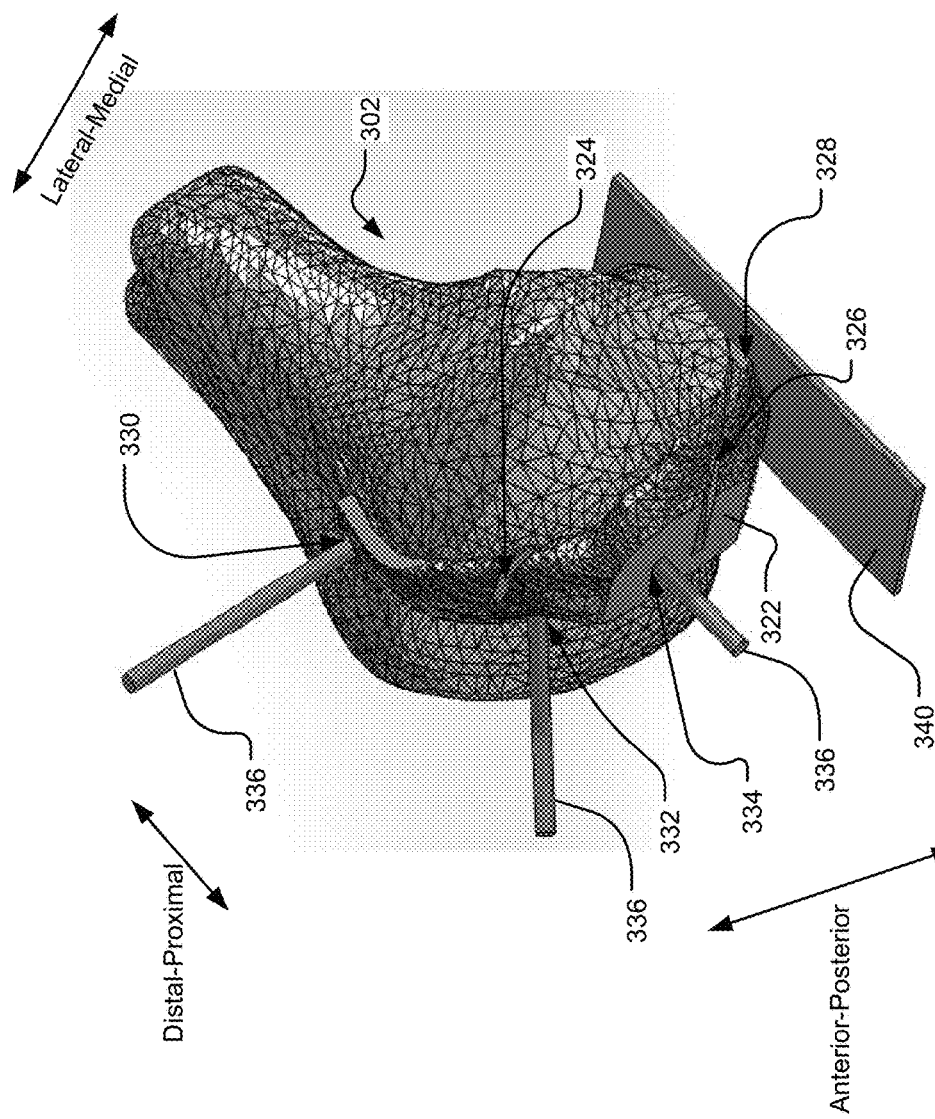
FIG. 10B depicts the same view as FIG. 10A with the resection or sawing instrument inserted into a posterior resection slot.
Figure 10C:
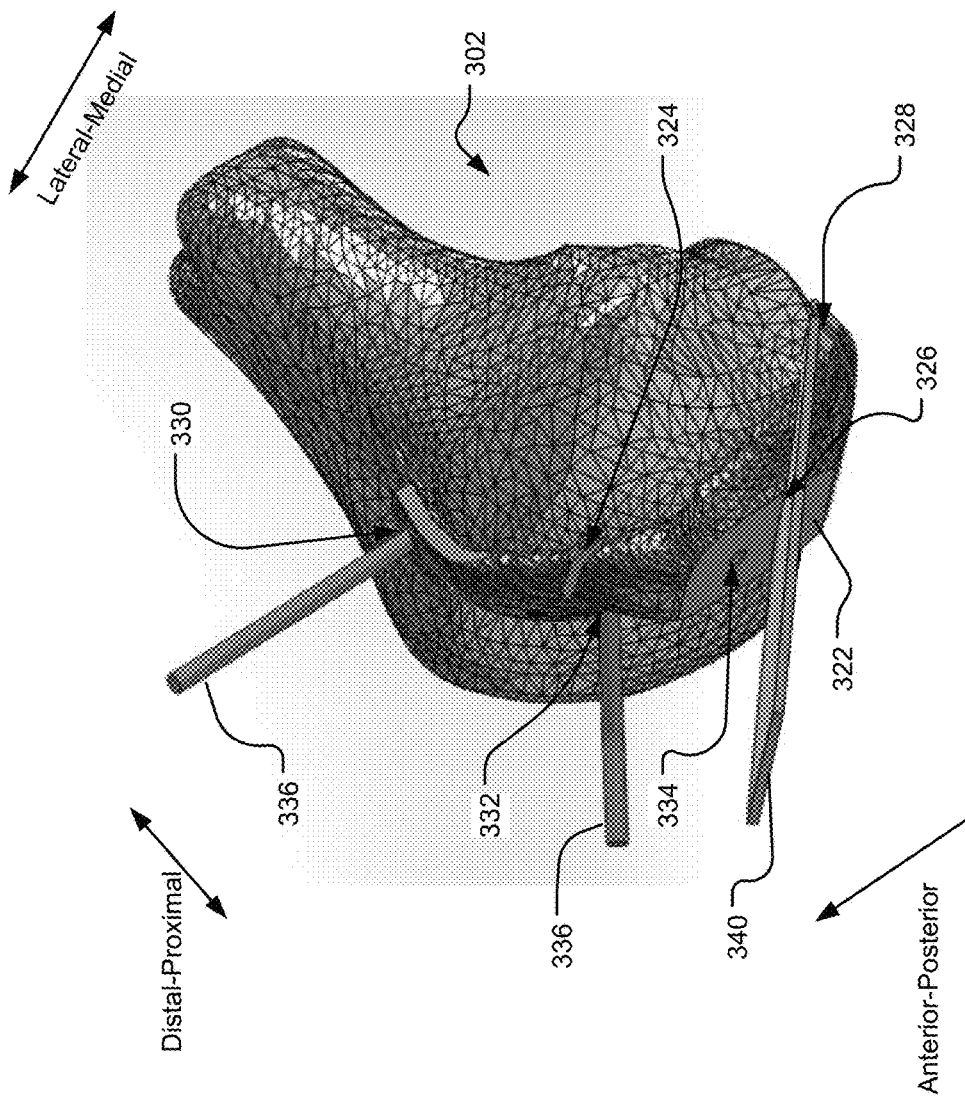
FIG. 10C depicts the same view as FIG. 10A with the resection or sawing instrument inserted into a chamfer resection slot.

Referring to FIGS. 10A-10C, which show a resection or sawing instrument 340 inserted into the distal resection slot 324, the posterior resection slot 328, and the chamfer resection slot 326, respectively, after checking the ligament balance, the knee is flexed to make resections in the femur 302. The distal resection slot 324 guides the distal resection of the patient femur 302, the posterior resection slot 328 guides the posterior resection of the patient femur 302, and the chamfer resection slot 326 guides the chamfer resection of the patient femur 302.

Figures 12A, 12B:
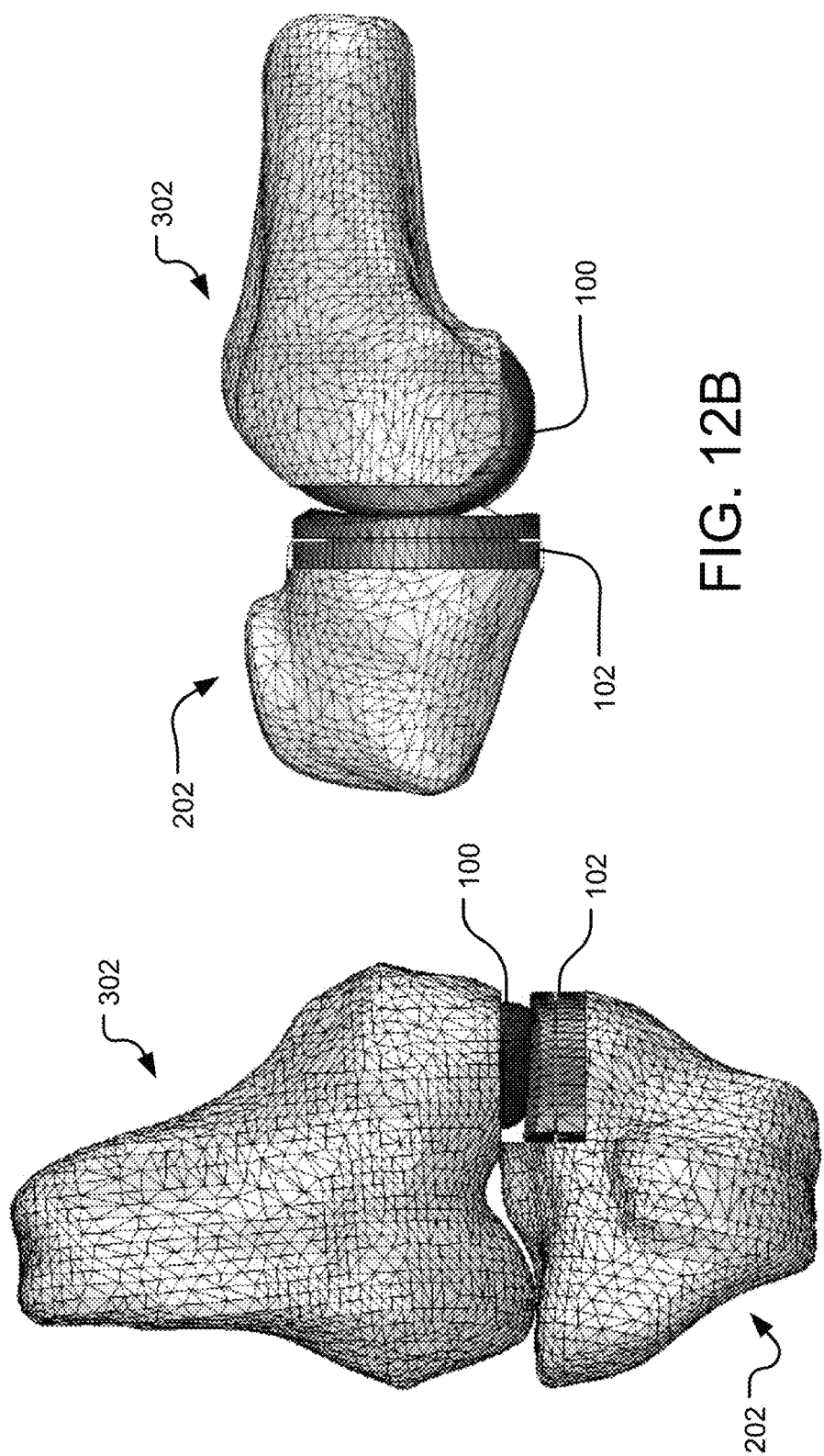
FIGS. 12A and 12B illustrate a coronal view and a sagittal view of the knee joint, respectively, showing trialing of the femoral and tibial implants.

As shown in FIG. 11, after the femur cutting guide 300 is removed, a distal resection 342, a chamfer resection 344, and a posterior resection 346 are complete, and the femur 302 is prepared to receive the femoral implant 100. After the femoral and tibial implants 100 and 102 are implanted on the femur 302 and tibia 202, respectively, trialing of the femoral and tibial implants 100 and 102 may be performed, as shown in FIGS. 12A and 12B.

Figure 13:
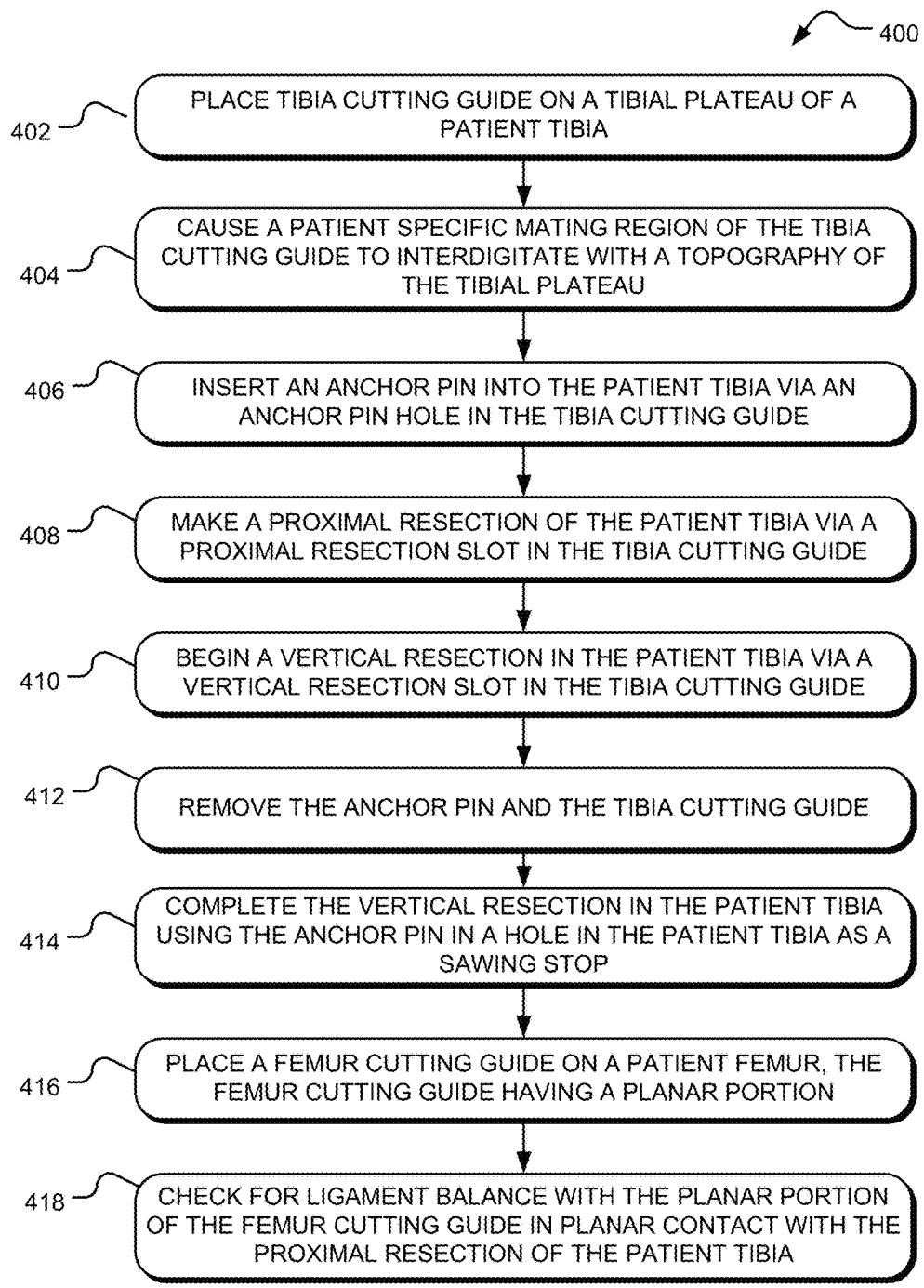
FIG. 13 is a flow chart showing example operations for performing treatment of the tibia for the tibial implant and of the femur for checking for ligament balance.

Turning to FIG. 13, example operations 400 for performing treatment of the tibia for the tibial implant and of the femur for checking for ligament balance are shown. A placing operation 402 places a tibia cutting guide on a tibial plateau of a patient tibia. In one implementation, the tibia cutting guide includes a patient specific mating region custom configured to interdigitate with a topography of the tibial plateau. To achieve this, the patient specific mating region may have surface contours that are a general negative image of surface contours of the tibial plateau.

The tibia cutting guide further includes a proximal resection slot and an anchor pin hole. In one implementation, the proximal resection slot includes an exterior opening that is defined in an exterior anterior surface of the tibia cutting guide. The proximal resection slot extends anterior-posterior and medial-lateral in the tibia cutting guide such that the proximal resection slot is configured to guide a proximal resection. In one implementation, the anchor pin hole includes an exterior opening that is defined in the exterior anterior surface of the tibia cutting guide. The anchor pin hole extends generally anterior-posterior through the tibia cutting guide and intersects with the proximal resection slot near a medial or later edge of the proximal resection slot. In one implementation, the tibia cutting guide includes a vertical resection slot having an exterior opening extending anterior-posterior and distal-proximal in the tibia cutting guide.

A causing operation 404 causes the patient specific mating region of the tibia cutting guide to interdigitate with the topography of the tibial plateau. An inserting operation 406 inserts an anchor pin into the patient tibia via the anchor pin hole such that the anchor pin is present within both the anchor pin hole and the patient tibia. With the patient specific mating region interdigitated with the topography of the tibial plateau, a making operation 408 makes a proximal resection of the patient tibia via the proximal resection slot. In one implementation, the making operation 408 uses the anchor pin as a sawing stop.

In one implementation, a beginning operation 410 at least begins a vertical resection in the patient tibia via the vertical resection slot. For example, the beginning operation 410 scores a vertical resection line in the patient tibia using the vertical resection slot as guidance. Once the making operation 408 and/or the beginning operation 410 are complete, a removing operation 412 removes the anchor pin from the tibia cutting guide. In one implementation, the removing operation 412 further removes the tibia cutting guide from the tibial plateau. A completing operation 414 reinserts the anchor pin into a hole in the patient tibia formerly occupied by the anchor pin when the anchor pin was present in both the anchor pin hole and the patient tibia. In one implementation, the completing operation 414 completes the vertical resection without the tibia cutting guide mounted on the patient tibia by using the anchor pin as a sawing stop. It will be appreciated by those skilled in the art that the completing operation 414 may comprise completing the proximal resection without the tibia cutting guide mounted on the patient tibia by using the anchor pin as a sawing stop in other implementations.

A placing operation 416 places a femur cutting guide on a condylar region of a patient femur. In one implementation, the femur cutting guide includes a custom mating region having a topography that makes interdigitating surface engagement with a topography of the condylar region. The femur cutting guide further includes a planar portion generally parallel with and distally offset from a distal resection slot of the femur cutting guide. A checking operation 418 places the planar portion of the femur cutting guide in planar contact with the proximal resection made during the making operation 408. The checking operation 418 checks for ligament balance with the planar portion in planar contact with the proximal resection.

Figure 14:
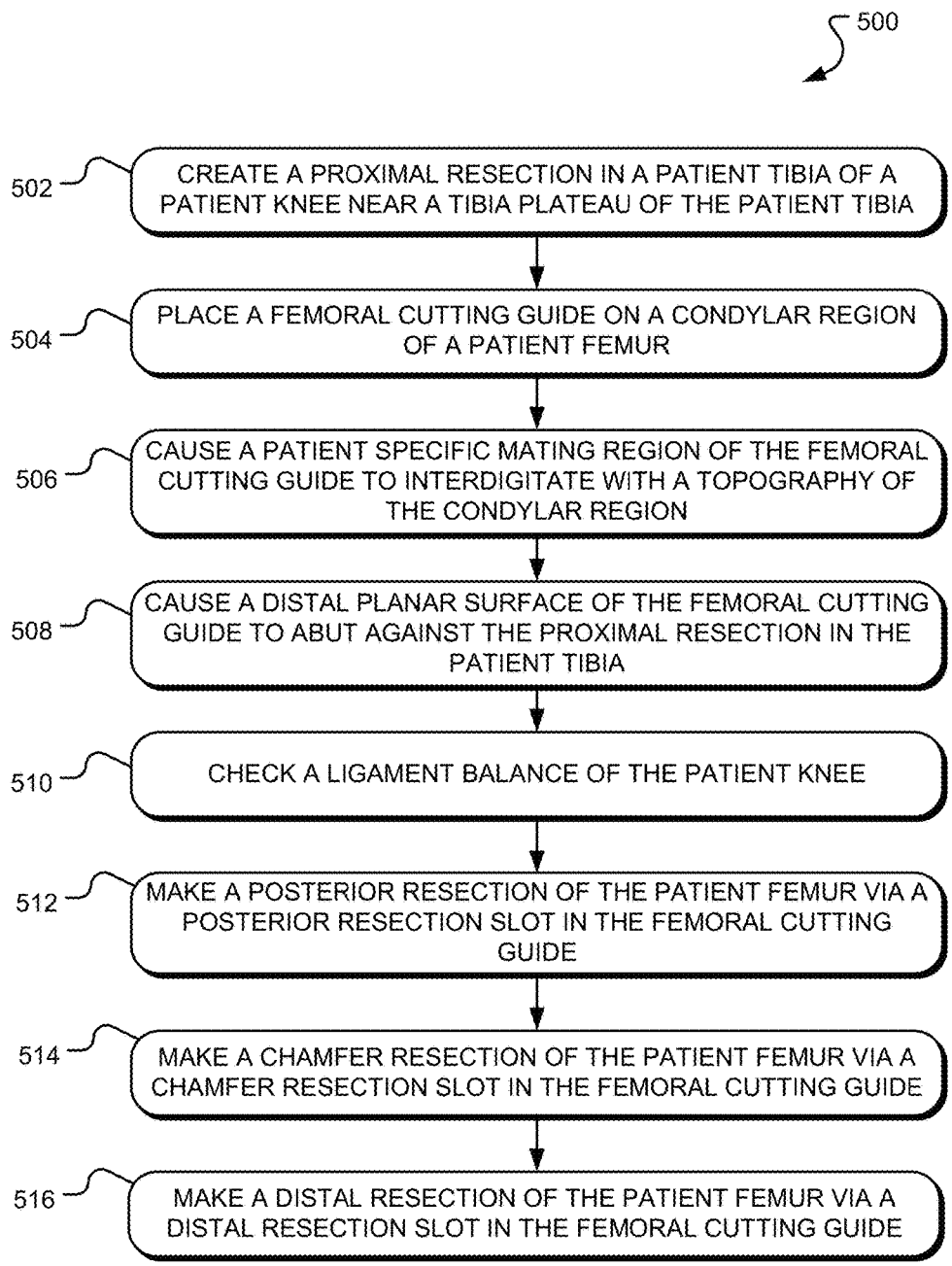
FIG. 14 is a flow chart showing example operations for performing treatment of the femur for the femoral implant.

FIG. 14 is a flow chart showing example operations 500 for performing treatment of the femur for the femoral implant. In one implementation, a creating operation 502 creates a proximal resection in a patient tibia near a tibial plateau of the patient tibia. For example, the creating operation 502 may create the proximal resection according to the operations 402-408 described with respect to FIG. 13.

A placing operation 504 places a femoral cutting guide on a condylar region of a patient femur. In one implementation, the femoral cutting guide includes a patient specific mating region, a distal resection slot, and a distal planar surface. The patient specific mating region is custom configured to interdigitate with a topography of the condylar region, and the patient specific mating region has surface contours that are a general negative image of surface contours of the condylar region. The distal resection slot includes an exterior opening defined in an exterior anterior surface of the femoral cutting guide, and the distal resection slot extends anterior-posterior and medial-lateral in the femoral cutting guide. The distal planar surface is generally parallel to the distal resection slot and distally spaced apart from the distal resection surface. In one implementation, the femoral cutting guide further includes a posterior resection slot configured to guide a posterior resection of the patient femur. In another implementation, the femoral cutting guide further includes a chamfer resection slot configured to guide a chamfer resection of the patient femur.

A causing operation 508 causes the patient specific mating region to interdigitate with the topography of the condylar region. With the patient specific mating region interdigitated with the topography of the condylar region, a checking operation 510 causes the distal planar surface of the femoral cutting guide to abut against the proximal resection made in the creating operation 502. The checking operation 510 checks a ligament balance of the patient knee with the femoral cutting guide engaged with the condylar region and the proximal resection.

A first making operation 512 makes a posterior resection of the patient femur via the posterior resection slot. A second making operation 514 makes a chamfer resection of the patient femur via the chamfer resection slot, and a third making operation 516 makes a distal resection of the patient femur via the distal resection slot. In one implementation, prior to the second making operation 514 and the third making operation 516, during which the chamfer and distal resections are performed, a distal pin is removed from the femoral cutting guide.

The discussion provided herein is given in the context of a unicompartmental knee arthroplasty cutting guides. However, the disclosure herein is readily applicable to other arthroplasty cutting guides as well as total or unicompartmental arthroplasty procedures in the knee or other joint contexts. Thus, the disclosure provided herein should be considered as encompassing cutting guides and the use thereof for both total and unicompartmental arthroplasty procedures. Additionally, the discussion given herein is applicable to cutting guides and methods applicable to restoring the patient to his or her natural alignment and also to cutting guides and methods applicable to arthroplasty procedures causing the patient's knee to be zero mechanical axis. Further, the discussion herein should be considered to encompass both medial and lateral unicompartmental cutting guides and arthroplasty procedures.

Various modifications and additions can be made to the exemplary embodiments discussed without departing from the spirit and scope of the presently disclosed technology. For example, while the embodiments described above refer to particular features, the scope of this disclosure also includes embodiments having different combinations of features and embodiments that do not include all of the described features. Accordingly, the scope of the presently disclosed technology is intended to embrace all such alternatives, modifications, and variations together with all equivalents thereof.

The invention claimed is:

1. An arthroplasty system for making resections in a knee region of a patient tibia in preparing a patient knee for the implantation of a tibial implant, the knee region including surface topography including surface contours of a tibial plateau surface including a medial and lateral surface, the arthroplasty system comprising:
   a) a cutting guide configured to facilitate resections in the tibial plateau surface and comprising:
      i) a patient specific mating region custom configured to interdigitate with a portion of the surface topography of the knee region and comprising surface contours that are a general negative image of the surface contours of the tibial plateau surface;
      ii) a proximal resection slot comprising an exterior opening defined in an exterior anterior surface of the cutting guide, the proximal resection slot extending anterior-posterior and medial-lateral in the cutting guide and configured to guide a proximal resection in the knee region when the patient specific mating region interdigitates with the portion of the surface topography of the knee region such that the surface contours of the mating region make corresponding surface contact with the surface contours of the tibial plateau surface; and
      iii) an anchor pin hole comprising an exterior opening defined in the exterior anterior surface of the cutting guide, the anchor pin hole extending generally anterior-posterior through the cutting guide and intersecting the proximal resection slot near a medial or lateral edge of the proximal resection slot; and
   b) an anchor pin comprising an elongated shaft configured to be received in the anchor pin hole in securing the cutting guide to the patient tibia.

2. The arthroplasty system of claim 1, wherein the anchor pin hole defines the medial or lateral edge of the proximal resection slot.

3. The arthroplasty system of claim 1, wherein the anchor pin hole is substantially coplanar with the proximal resection slot.

4. The arthroplasty system of claim 1, wherein the anchor pin hole includes a longitudinal center axis that is substantially centered distal-proximal relative to a distal-proximal thickness of the proximal resection slot.

5. The arthroplasty system of claim 1, wherein, when the anchor pin is received in the anchor pin hole, the anchor pin serves as a sawing stop.

6. The arthroplasty system of claim 1, further comprising a vertical resection slot comprising an exterior opening defined in an exterior proximal surface of the cutting guide, the vertical resection slot extending anterior-posterior and distal-proximal in the cutting guide and configured to guide a vertical resection in the knee region when the patient specific mating region interdigitates with the portion of the topography of the knee region such that the surface contours of the mating region make corresponding surface contact with the surface contours of the tibial plateau surface.

7. The arthroplasty system of claim 6, wherein the anchor pin hole is substantially coplanar with the vertical resection slot but the anchor pin hole and vertical resection slot do not intersect.

8. The arthroplasty system of claim 6, wherein the anchor pin hole includes a longitudinal center axis that is substantially centered medial-lateral relative to a medial-lateral thickness of the vertical resection slot.

9. The arthroplasty system of claim 1, wherein the elongated shaft is configured to be received in the anchor pin hole in an interference fit.

10. The arthroplasty system of claim 1, wherein the cutting guide is a unicompartmental cutting guide configured to facilitate a resection in one of the medial or lateral surfaces of the tibial plateau surface.

11. A method of performing a knee arthroplasty, the method comprising:
 a) place a tibia cutting guide on a tibial plateau of a patient tibia, the tibia cutting guide comprising: i) a patient specific mating region custom configured to interdigitate with a portion of a surface topography of the tibial plateau and comprising surface contours that are a general negative image of surface contours of the tibial plateau; ii) a proximal resection slot comprising an exterior opening defined in an exterior anterior surface of the tibia cutting guide, the proximal resection slot extending anterior-posterior and medial-lateral in the tibia cutting guide; and iii) an anchor pin hole comprising an exterior opening defined in the exterior anterior surface of the tibia cutting guide, the anchor pin hole extending generally anterior-posterior through the tibia cutting guide and intersecting the proximal resection slot near a medial or lateral edge of the proximal resection slot;
 b) cause the patient specific mating region to interdigitate with the topography of the tibial plateau;
 c) insert an anchor pin into the patient tibia via the anchor pin hole such that the anchor pin is present within both the anchor pin hole and the patient tibia; and
 d) with the mating region interdigitated with the topography of the tibial plateau, make a proximal resection of the patient tibia via the proximal resection slot.

12. The method of claim 11, wherein the anchor pin hole defines the medial or lateral edge of the proximal resection slot.

13. The method of claim 11, wherein the tibia cutting guide further comprises a vertical resection slot comprising an exterior opening defined in an exterior proximal surface of the cutting guide, the vertical resection slot extending anterior-posterior and distal-proximal in the cutting guide, the method further comprising at least beginning a vertical resection in the patient tibia via the vertical resection slot when the mating region is interdigitated with the topography of the tibial plateau.

14. The method of claim 11, wherein the cutting guide is a unicompartmental cutting guide configured to facilitate a resection in one of the medial or lateral surfaces of the tibial plateau.

15. An arthroplasty system for making resections in a patient bone of a joint in preparing the patient bone for the implantation of an implant, the patient bone including an end having surface topography including surface contours of a medial portion and a lateral portion, the arthroplasty system comprising:
 a) a cutting guide configured to facilitate resections in the end of the patient bone and comprising:
  i) a patient specific mating region custom configured to interdigitate with a portion of the surface contours of the surface topography of the end of the patient bone, the patient specific mating region comprising surface contours that are a general negative image of the portion of the surface contours of the surface topography of the end of the patient bone;
  ii) a resection slot comprising an exterior opening defined in an exterior anterior surface of the cutting guide, the resection slot extending anterior-posterior and medial-lateral in the cutting guide and configured to guide a resection in the patient bone when the patient specific mating region interdigitates with the portion of the surface contours of the surface topography of the end of the patient bone; and
  iii) an anchor pin hole comprising an exterior opening defined in the exterior anterior surface of the cutting guide, the anchor pin hole extending generally anterior-posterior through the cutting guide and intersecting the resection slot near a medial or lateral edge of the resection slot; and
 b) an anchor pin comprising an elongated shaft configured to be received in the anchor pin hole in securing the cutting guide to the patient bone.

16. The arthroplasty system of claim 15, further comprising a vertical resection slot comprising an exterior opening defined in an exterior proximal surface of the cutting guide, the vertical resection slot extending anterior-posterior and distal-proximal in the cutting guide and configured to guide a vertical resection in the patient bone when the patient specific mating region interdigitates with the portion of the surface contours of the surface topography of the end of the patient bone.

17. The arthroplasty system of claim 16, wherein the anchor pin hole is substantially coplanar with the vertical resection slot but the anchor pin hole and vertical resection slot do not intersect.

18. The arthroplasty system of claim 16, wherein the anchor pin hole includes a longitudinal center axis that is substantially centered medial-lateral relative to a medial-lateral thickness of the vertical resection slot.

19. The arthroplasty system of claim 15, wherein the patient bone is that of a tibia, and the resection slot is a proximal resection slot.

20. The arthroplasty system of claim 15, wherein the cutting guide is a unicompartmental cutting guide configured to facilitate a resection in one of the medial or lateral portions of the patient bone.

* * * * *